(12) United States Patent
Hasegawa et al.

(10) Patent No.: US 6,280,898 B1
(45) Date of Patent: Aug. 28, 2001

(54) LACTONE-CONTAINING COMPOUNDS, POLYMERS, RESIST COMPOSITIONS, AND PATTERNING METHOD

(75) Inventors: Koji Hasegawa; Tsunehiro Nishi; Takeshi Kinsho; Jun Hatakeyama; Osamu Watanabe, all of Nakakubiki-gun (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 62 days.

(21) Appl. No.: 09/404,763

(22) Filed: Sep. 24, 1999

(30) Foreign Application Priority Data

Sep. 25, 1998 (JP) .................................................. 10-270373

(51) Int. Cl.[7] ............................ G03F 7/004; G08F 10/00; C07D 307/00
(52) U.S. Cl. ........................ 430/270.1; 430/326; 526/281; 549/45; 549/300
(58) Field of Search ................................ 430/270.1, 325, 430/326, 296; 549/300, 45; 526/281

(56) References Cited

U.S. PATENT DOCUMENTS

| | | | | |
|---|---|---|---|---|
| 4,018,767 | * | 4/1977 | Buyniski et al. | 260/247.2 A |
| 4,166,915 | * | 9/1979 | Buchholz | 568/820 |
| 4,188,219 | * | 2/1980 | Cawley | 430/208 |
| 5,185,143 | * | 2/1993 | Cohen | 424/47 |
| 5,541,344 | * | 7/1996 | Becker et al. | 549/300 |
| 5,811,462 | * | 9/1998 | Hungate et al. | 514/616 |
| 5,910,392 | * | 6/1999 | Nozaki et al. | 430/270.1 |
| 6,008,306 | * | 12/1999 | Hafner et al. | 526/171 |
| 6,057,083 | * | 5/2000 | Taylor et al. | 430/326 |

\* cited by examiner

*Primary Examiner*—Janet Baxter
*Assistant Examiner*—Rosemary Ashton
(74) *Attorney, Agent, or Firm*—Millen, White, Zelano & Branigan, P.C.

(57) ABSTRACT

A novel lactone-containing compound is provided as well as a polymer comprising units of the compound. The polymer is used as a base resin to formulate a resist composition having a high sensitivity, resolution and etching resistance.

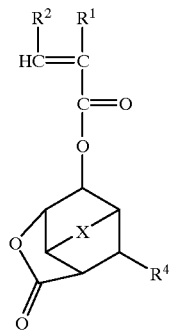

$X = CH_2, CH_2CH_2, O, S.$

21 Claims, No Drawings

LACTONE-CONTAINING COMPOUNDS, POLYMERS, RESIST COMPOSITIONS, AND PATTERNING METHOD

This invention relates to (1) a compound having a specific lactone-containing structure, (2) a polymer comprising units of the compound which is blended as a base resin to formulate a resist composition having improved substrate adhesion, adequate penetration of developer, and high etching resistance, and especially suited as micropatterning material for VLSI fabrication, (3) a method for preparing the polymer, (4) a resist composition comprising the polymer, and (5) a patterning method using the resist composition.

BACKGROUND OF THE INVENTION

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF or ArF excimer laser as the light source is strongly desired to reach the practical level as the micropatterning technique capable of achieving a feature size of 0.3 µm or less.

As the base resin in a resist material having high transmittance to light of an excimer laser, especially ArF excimer laser having a wavelength of 193 nm, polyacrylic or polymethacrylic acid derivatives and polymers comprising aliphatic cyclic compounds such as norbornene-maleic anhydride copolymers in the backbone are used. For the base resin used in chemical amplification type resist compositions, not only an acid liability closely related to resolution, but also etching resistance and substrate adhesion are required. In the above-described resins, it is intended to accomplish such distinct characteristics by using a plurality of monomers having different properties to form a complex copolymer. However, these resins are not yet satisfactory on the practical level.

More particularly, monomers having as suspending groups polycyclic hydrocarbon groups such as adamantyl, tricyclodecyl and norbornyl are used for imparting etching resistance, and monomers having as suspending groups polar groups such as hydroxyl and carboxyl groups are used for imparting substrate adhesion. However, in a system where an extremely hydrophobic monomer for imparting etching resistance and an extremely hydrophilic monomer for imparting substrate adhesion are admixed, it is difficult to effect uniform polymerization reaction. Due to side reaction, homopolymers and undesired block copolymers can form. If the polymer product thus obtained is blended in a resist composition, this resist suffers from drawbacks including uneven dissolution due to in-film delamination, pattern collapse due to peeling of highly hydrophobic sites, and swelling due to random penetration of a liquid developer to highly hydrophilic sites. Even though the etching resistance is improved, the resolution of the resist is extremely reduced.

SUMMARY OF THE INVENTION

An object of the invention is to provide (1) a lactone-containing compound capable of forming a polymer possessing a well-balanced profile of etching resistance and substrate adhesion, (2) a polymer comprising units of the compound which is blended as a base resin to formulate a resist composition having significantly improved resolution and etching resistance over prior art compositions, (3) a method for preparing the polymer, (4) a resist composition comprising the polymer as a base resin, and (5) a patterning method using the resist composition.

We have found that a novel lactone-containing compound of the general formula (1) obtained by a method to be described later is useful as a starting reactant from which a polymer possessing both etching resistance and substrate adhesion is prepared; that a resist composition using as the base resin a novel polymer obtained from the compound and having a weight average molecular weight of 1,000 to 500,000 is improved in resolution and etching resistance; and that the resist composition is very useful in precise microfabrication.

In a first aspect, the invention provides a lactone-containing compound of the following general formula (1):

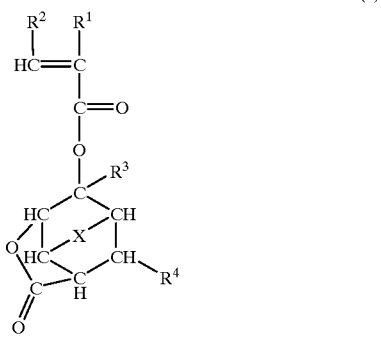

(1)

wherein $R^1$ is hydrogen, methyl or $CH_2CO_2R^5$, $R^2$ is hydrogen, methyl or $CO_2R^5$, $R^3$ is a straight, branched or cyclic alkyl group of 1 to 8 carbon atoms, $R^4$ is hydrogen or $CO_2R^5$, $R^5$ is a straight, branched or cyclic alkyl group of 1 to 15 carbon atoms, and X is $CH_2$, $CH_2CH_2$, O or S.

In a second aspect, the invention provides a polymer comprising units of the following general formula (1a) and having a weight average molecular weight of 1,000 to 500,000,

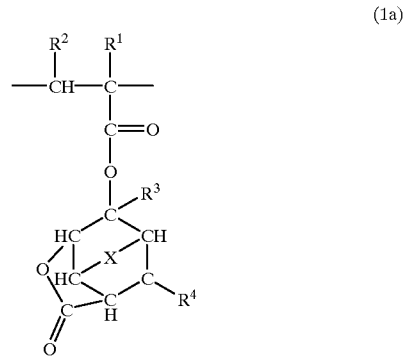

(1a)

wherein $R^1$ to $R^4$ and X are as defined above.

The polymer may further include units of at least one of the following general formulae (2a) to (10a).

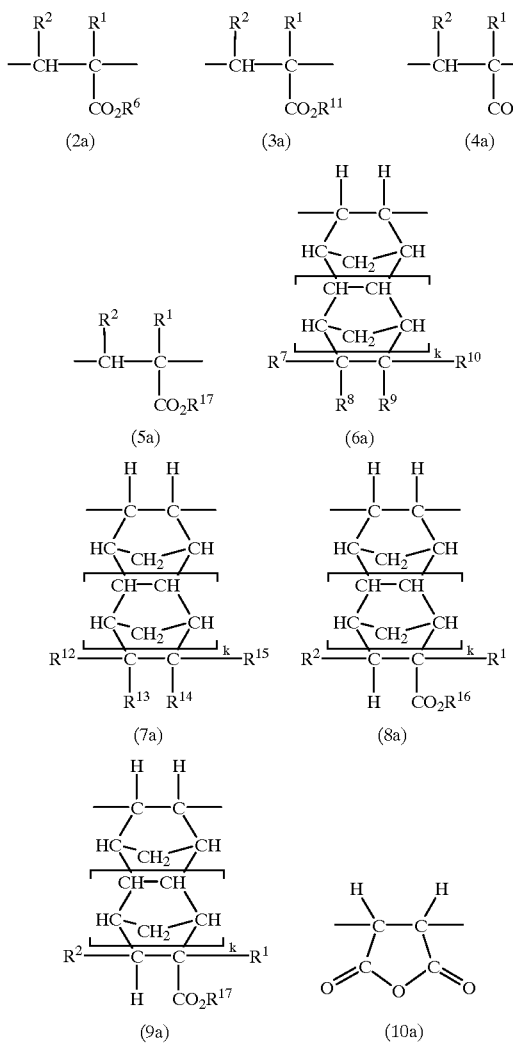

Herein, $R^1$ and $R^2$ are as defined above, $R^6$ is hydrogen or a carboxyl or hydroxyl-containing monovalent hydrocarbon group of 1 to 15 carbon atoms, at least one of $R^7$ to $R^{10}$ is a carboxyl or hydroxyl-containing monovalent hydrocarbon group of 1 to 15 carbon atoms, and the remainder are independently hydrogen or a straight, branched or cyclic alkyl group of 1 to 15 carbon atoms, or $R^7$ to $R^{10}$, taken together, may form a ring, and when they form a ring, at least one of $R^7$ to $R^{10}$ is a carboxyl or hydroxyl-containing divalent hydrocarbon group of 1 to 15 carbon atoms, and the remainder are independently a single bond or a straight, branched or cyclic alkylene group of 1 to 15 carbon atoms, $R^{11}$ is a monovalent hydrocarbon group of 3 to 15 carbon atoms containing a —$CO_2$— partial structure, at least one of $R^{12}$ to $R^{15}$ is a monovalent hydrocarbon group of 2 to 15 carbon atoms containing a —$CO_2$— partial structure, and the remainder are independently hydrogen or a straight, branched or cyclic alkyl group of 1 to 15 carbon atoms, or $R^{12}$ to $R^{15}$, taken together, may form a ring, and when they form a ring, at least one of $R^{12}$ to $R^{15}$ is a divalent hydrocarbon group of 1 to 15 carbon atoms containing a —$CO_2$— partial structure, and the remainder are independently a single bond or a straight, branched or cyclic alkylene group of 1 to 15 carbon atoms, $R^{16}$ is a polycyclic hydrocarbon group of 7 to 15 carbon atoms or an alkyl group containing such a polycyclic hydrocarbon group, $R^{17}$ is an acid labile group, and k is equal to 0 or 1.

In a third aspect, the invention provides a method for preparing a polymer, comprising effecting radical or anionic polymerization between a lactone-containing compound of the general formula (1) and another compound having a carbon-to-carbon double bond.

In a fourth aspect, the invention provides a resist composition comprising the polymer defined above. Preferably, the resist composition further includes a photoacid generator capable of generating an acid upon exposure to high-energy radiation or electron beams, and an organic solvent.

In a fifth aspect, the invention provides a method for forming a resist pattern comprising the steps of (i) applying the resist composition onto a substrate to form a film, (ii) heat treating the film and then exposing it to high-energy radiation or electron beams through a photo mask, and (iii) optionally heat treating the exposed film and developing it with a developer.

The polymer or high molecular weight compound comprising units of the lactone-containing compound of formula (1) has a high etching resistance and sufficient substrate adhesion and eliminates the drawbacks of prior art resist materials including uneven dissolution due to in-film delamination, pattern collapse due to peeling of highly hydrophobic sites, and swelling due to random penetration of a liquid developer to highly hydrophilic sites.

The lactone-containing compound of formula (1) possesses both polarity attributable to the lactone structure and rigidity attributable to the fused tricyclic structure within a common molecule. When copolymerization is effected using this lactone-containing compound, there is obtained a uniform polymer exhibiting a satisfactory dissolution behavior in that separation between hydrophilic sites and hydrophobic sites does not occur as a matter of principle. In the polymer thus obtained, lactone sites can move relatively freely at a position spaced apart from the backbone so that a degree of substrate adhesion corresponding to the amount of lactone introduced may be effectively exerted. Not only the rigidity of the fused tricyclic structure imparts a sufficient etching resistance to the polymer, but its hydrophobic property moderately mitigates the affinity of lactone sites to a liquid developer, thereby avoiding swelling by excessive penetration of the developer and achieving an improvement in the rectangularity of a pattern. Accordingly, a resist composition having the polymer blended therein as the base resin forms a resist pattern having improved rectangularity and is etching resistance and free of peeling.

DESCRIPTION OF THE PREFERRED EMBODIMENTS

Lactone-containing compound

In the first aspect of the invention, the novel lactone-containing compounds is represented by the following general formula (1).

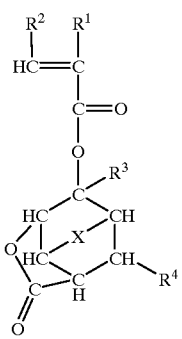
(1)

Herein, $R^1$ is hydrogen, methyl or $CH_2CO_2R^5$ wherein $R^5$ is defined later. $R^2$ is hydrogen, methyl or $CO_2R^5$. $R^3$ is a straight, branched or cyclic alkyl group of 1 to 8 carbon atoms, examples of which include methyl, ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl, and cyclohexylethyl. $R^4$ is hydrogen or $CO_2R^5$. $R^5$ is a straight, branched or cyclic alkyl group of 1 to 15 carbon atoms, examples of which include methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, and butyladamantyl. X is $CH_2$, $CH_2CH_2$, O or S.

The lactone-containing compounds can be prepared by the following exemplary procedure although the preparatory procedure is not limited thereto.

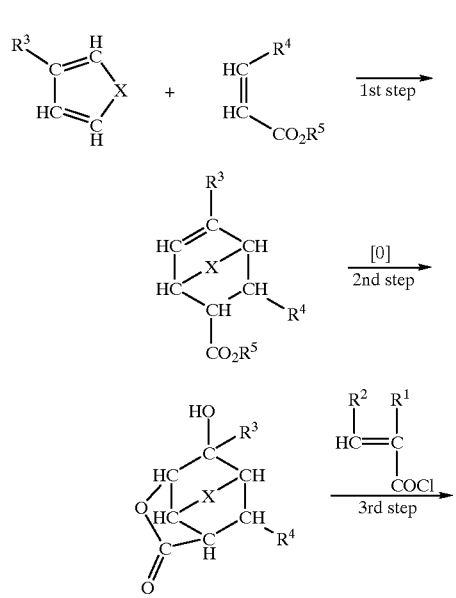
(1)

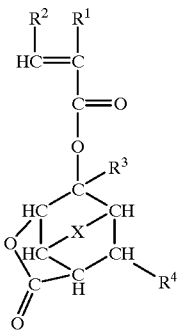

Herein, $R^1$ to $R^5$ and X are as defined above.

The first step is the Diels-Alder reaction. The reaction readily takes place under well-known conditions. Preferably reaction is carried out in a solventless system or in benzene or suitable solvents, optionally in the presence of a catalyst such as boron trifluoride and also optionally under heat.

The second step is oxidation of a double bond accompanied by lactonization. The reaction readily takes lo place under well-known conditions. Preferably reaction is carried out using formic acid as a solvent and reactant and hydrogen peroxide as an oxidizing agent, optionally under cooling.

The third step is esterification. The reaction readily takes place under well-known conditions. Preferably reaction is carried out in a solvent such as methylene chloride by sequentially or simultaneously adding a carboxylic halide such as acrylic chloride or methacrylic chloride and a base such as triethylamine thereto, optionally under cooling.

Several illustrative, non-limiting examples of the lactone-containing compound are given below.

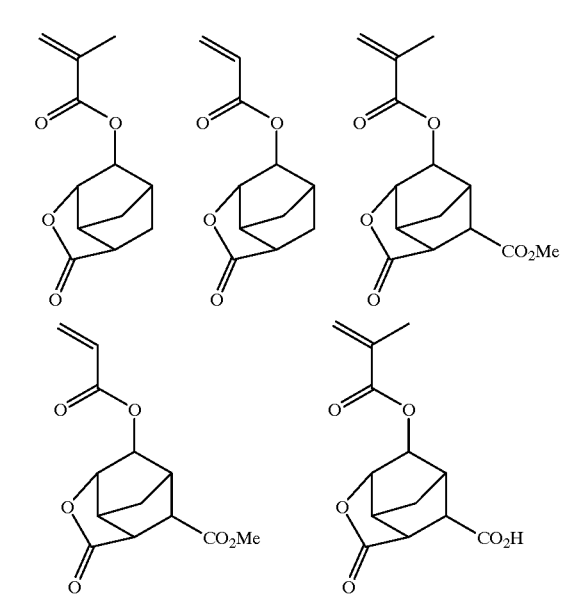

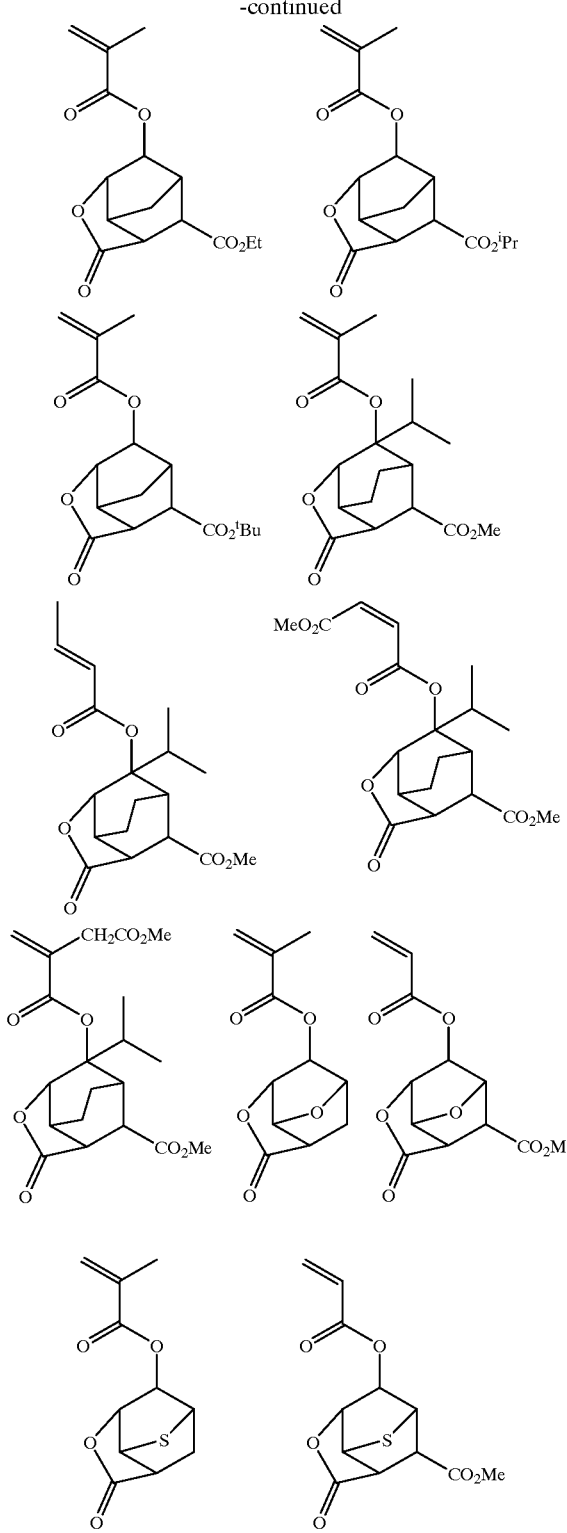

Herein, Me is methyl, Et is ethyl, $^i$Pr is isopropyl, and $^t$Bu is tert-butyl.

In the second aspect of the invention, there is provided a polymer or high molecular weight compound which is obtained using the lactone-containing compound of formula (1) as a monomer. The polymer is characterized by comprising units of the following general formula (1a) and having a weight average molecular weight of 1,000 to 500,000, and preferably 5,000 to 100,000.

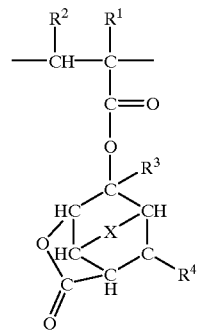

(1a)

Herein, $R^1$ to $R^4$ and X are as defined above.

In addition to the units of formula (1a), the polymer may further include units of at least one of the following general formulae (2a) to (10a) which are derived from monomers of the following general formulae (2) to (10).

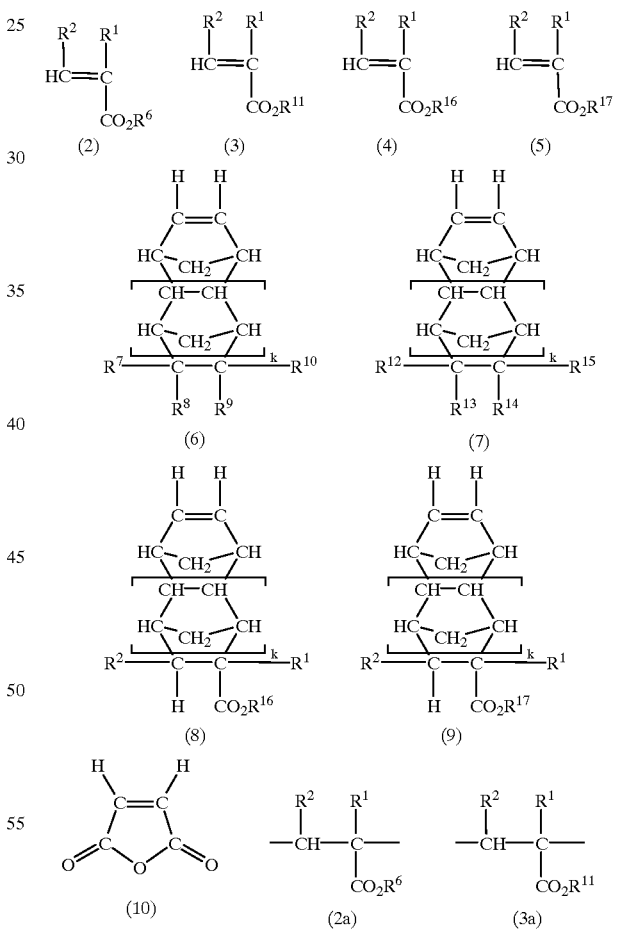

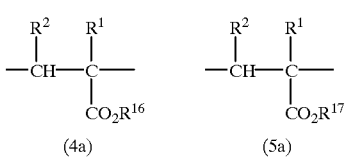

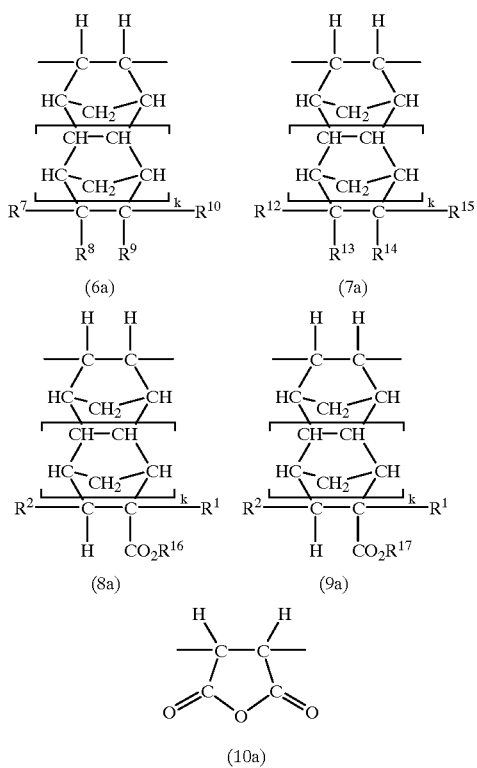

(6a) (7a) (8a) (9a) (10a)

In the above formulae, k is equal to 0 or 1. Then the formulae (6a) to (9a) may also be represented by the following formulae (6a-1) to (9a-2).

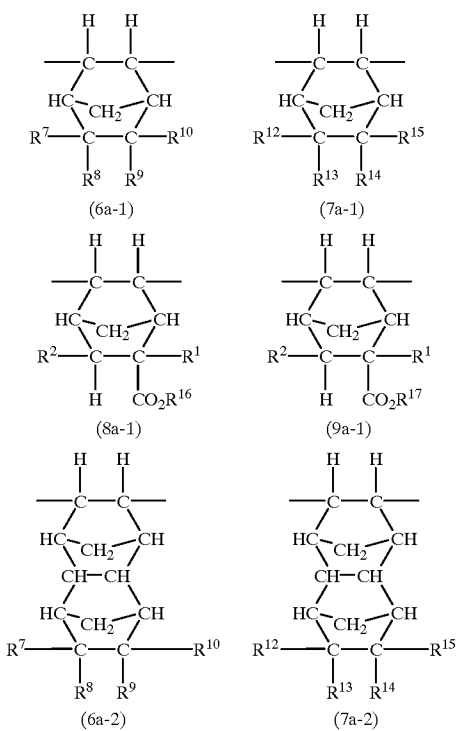

(6a-1) (7a-1) (8a-1) (9a-1) (6a-2) (7a-2)

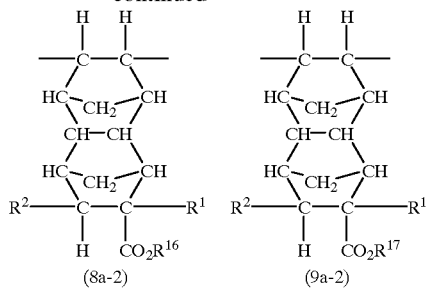

(8a-2) (9a-2)

In the above formulae, $R^1$ and $R^2$ are as defined above.

$R^6$ represents hydrogen or a carboxyl or hydroxyl-containing monovalent hydrocarbon group of 1 to 15 carbon atoms, preferably a carboxyl or hydroxyl-containing straight, branched or cyclic alkyl group. Examples include carboxyethyl, carboxybutyl, carboxycyclopentyl, carboxycyclohexyl, carboxynorbornyl, carboxyadamantyl, hydroxyethyl, hydroxybutyl, hydroxycyclopentyl, hydroxycyclohexyl, hydroxynorbornyl, and hydroxyadamantyl.

At least one of $R^7$ to $R^{10}$ is a carboxyl or hydroxyl-containing monovalent hydrocarbon group of 1 to 15 carbon atoms, preferably a carboxyl or hydroxyl-containing straight, branched or cyclic alkyl group, and the remainder are independently hydrogen or a straight, branched or cyclic alkyl group of 1 to 15 carbon atoms. Examples of the carboxyl or hydroxyl-containing monovalent C1–C15 hydrocarbon group include carboxy, carboxymethyl, carboxyethyl, carboxybutyl, hydroxymethyl, hydroxyethyl, hydroxybutyl, 2-carboxyethoxycarbonyl, 4-carboxybutoxycarbonyl, 2-hydroxyethoxycarbonyl, 4-hydroxybutoxycarbonyl, carboxycyclopentyloxycarbonyl, carboxycyclohexyloxycarbonyl, carboxynorbornyloxycarbonyl, carboxyadamantyloxycarbonyl, hydroxycyclopentyloxycarbonyl, hydroxycyclohexyloxycarbonyl, hydroxynorbornyloxycarbonyl, and hydroxyadamantyloxycarbonyl. Examples of the straight, branched or cyclic C1–C15 alkyl group are the same as exemplified for $R^5$. Alternatively, $R^7$ to $R^{10}$, taken together, may form a ring. When they form a ring, at least one of $R^7$ to $R^{10}$ is a carboxyl or hydroxyl-containing divalent hydrocarbon group of 1 to 15 carbon atoms, preferably a carboxyl or hydroxyl-containing straight or branched alkylene group, and the remainder are independently a single bond or a straight, branched or cyclic alkylene group of 1 to 15 carbon atoms. Examples of the carboxyl or hydroxyl-containing divalent C1–C15 hydrocarbon group are those exemplified for the carboxyl or hydroxyl-containing monovalent hydrocarbon group, with one hydrogen atom being eliminated therefrom. Examples of the straight, branched or cyclic C1–C15 alkylene group are those exemplified for $R^5$, with one hydrogen atom being eliminated therefrom.

$R^{11}$ is a monovalent hydrocarbon group of 3 to 15 carbon atoms containing a —$CO_2$— partial structure. Examples include 2-oxooxolan-3-yl, 4,4-dimethyl-2-oxooxolan-3-yl, 4-methyl-2-oxooxan-4-yl, 2-oxo-1,3-dioxolan-4-ylmethyl, and 5-methyl-2-oxooxolan-5-yl.

At least one of $R^{12}$ to $R^{15}$ is a monovalent hydrocarbon group of 2 to 15 carbon atoms containing a —$CO_2$— partial structure, and the remainder are independently hydrogen or a straight, branched or cyclic alkyl group of 1 to 15 carbon atoms. Examples of the monovalent C2–C15 hydrocarbon group containing a —CO$_2$— partial structure include 2-oxooxolan-3-yloxycarbonyl, 4,4-dimethyl-2-oxooxolan-3-yloxycarbonyl, 4-methyl-2-oxooxan-4-yloxycarbonyl, 2-oxo-1,3-dioxolan-4-ylmethyloxycarbonyl, and 5-methyl-2-oxooxolan-5-yloxycarbonyl. Examples of the straight, branched or cyclic C1–C15 alkyl group are as exemplified for $R^5$. Alternatively, $R^{12}$ to $R^{15}$, taken together, may form a ring. When they form a ring, at least one of $R^{12}$ to $R^{15}$ is a divalent hydrocarbon group of 1 to 15 carbon atoms containing a —CO$_2$— partial structure, and the remainder are independently a single bond or a straight, branched or cyclic alkylene group of 1 to 15 carbon atoms. Examples of the divalent C1–C15 hydrocarbon group containing a —CO$_2$— partial structure include 1-oxo-2-oxapropane-1,3-diyl, 1,3-dioxo-2-oxapropane-1,3-diyl, 1-oxo-2-oxabutane-1,4-diyl, and 1,3-dioxo-2-oxabutane-1,4-diyl as well as those exemplified above for the monovalent hydrocarbon group containing a —CO$_2$— partial structure, with one hydrogen atom being eliminated therefrom. Examples of the straight, branched or cyclic C1–C15 alkylene group are those exemplified for $R^5$, with one hydrogen atom being eliminated therefrom.

$R^{16}$ is a polycyclic hydrocarbon group of 7 to 15 carbon atoms or an alkyl group containing such a polycyclic hydrocarbon group. Examples include norbornyl, bicyclo[3.3.1]nonyl, tricyclo[5.2.1.0$^{2,6}$]decyl, adamantyl, ethyladamantyl, butyladamantyl, norbornylmethyl, and adamantylmethyl.

$R^{17}$ is an acid labile group. Examples of the acid labile group include groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

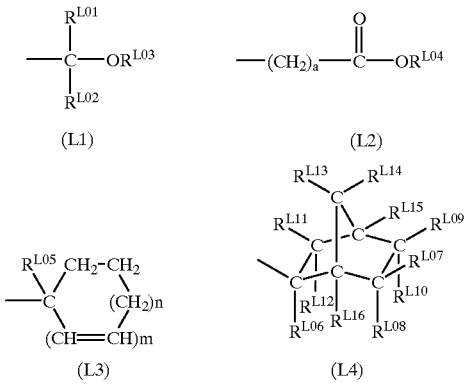

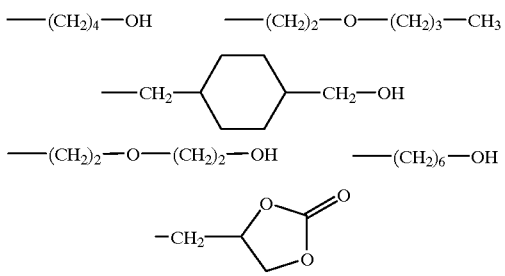

$R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, propyl, isopropyl, n-butyl, sec-butyl, tert-butyl, cyclopentyl, cyclohexyl, 2-ethylhexyl, and n-octyl. $R^{L03}$ is a monovalent hydrocarbon group of 1 to 18 carbon atoms, preferably 1 to 10 carbon atoms, which may contain a hetero atom such as oxygen, examples of which include unsubstituted straight, branched or cyclic alkyl groups and straight, branched or cyclic alkyl groups in which some hydrogen atoms are replaced by hydroxyl, alkoxy, oxo, amino, alkylamino or the like. Illustrative examples are the substituted alkyl groups shown below.

A pair of $R^{L01}$ and $R^{L02}$, $R^{L01}$ and $R^{L03}$, or $R^{L02}$ and $R^{L03}$ may form a ring. Each of $R^{L01}$, $R^{L02}$ and $R^{L03}$ is a straight or branched alkylene group of 1 to 18 carbon atoms, preferably 1 to 10 carbon atoms when they form a ring.

$R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, and 2-methyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-5-oxooxolan-4-yl. Letter a is an integer of 0 to 6.

$R^{L05}$ is a straight, branched or cyclic alkyl group of 1 to 8 carbon atoms or a substituted or unsubstituted aryl group of 6 to 20 carbon atoms. Examples of the straight, branched or cyclic alkyl group include methyl, ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl, and cyclohexylethyl. Exemplary aryl groups are phenyl, methylphenyl, naphthyl, anthryl, phenanthryl, and pyrenyl. Letter m is equal to 0 or 1, n is equal to 0, 1, 2 or 3, and 2m+n is equal to 2 or 3.

$R^{L06}$ is a straight, branched or cyclic alkyl group of 1 to 8 carbon atoms or a substituted or unsubstituted aryl group of 6 to 20 carbon atoms. Examples of these groups are the same as exemplified for $R^{L05}$.

$R^{L07}$ to $R^{L06}$ independently represent hydrogen or monovalent hydrocarbon groups of 1 to 15 carbon atoms which may contain a hetero atom. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted ones of these groups in which some hydrogen atoms are replaced by hydroxyl, alkoxy, carboxy, alkoxycarbonyl, oxo, amino, alkylamino, cyano, mercapto, alkylthio, sulfo or other groups. Alternatively, $R^{L07}$ to $R^{L16}$, taken together, may form a ring (for example, a pair of $R^{L07}$ and $R^{L08}$, $R^{L07}$ and $R^{L09}$, $R^{L08}$ and $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent C1–C15 hydrocarbon group which may contain a hetero atom, when they form a ring, examples of which are the ones exemplified above for the monovalent hydrocarbon groups, with one hydrogen atom being eliminated. Two of $R^{L07}$ to $R^{L16}$ which are attached to adjoining carbon atoms (for example, a pair of $R^{L07}$ and $R^{L09}$, $R^{L09}$ and $R^{L15}$, $R^{L13}$ and $R^{L15}$, or a similar pair) may bond together directly to form a double bond.

Of the acid labile groups of formula (L1), the straight and branched ones are exemplified by the following groups.

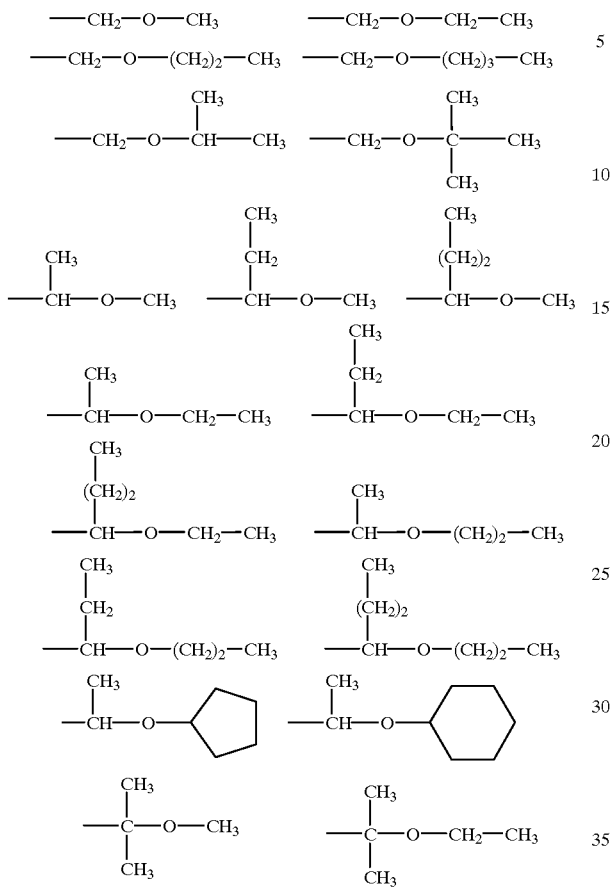

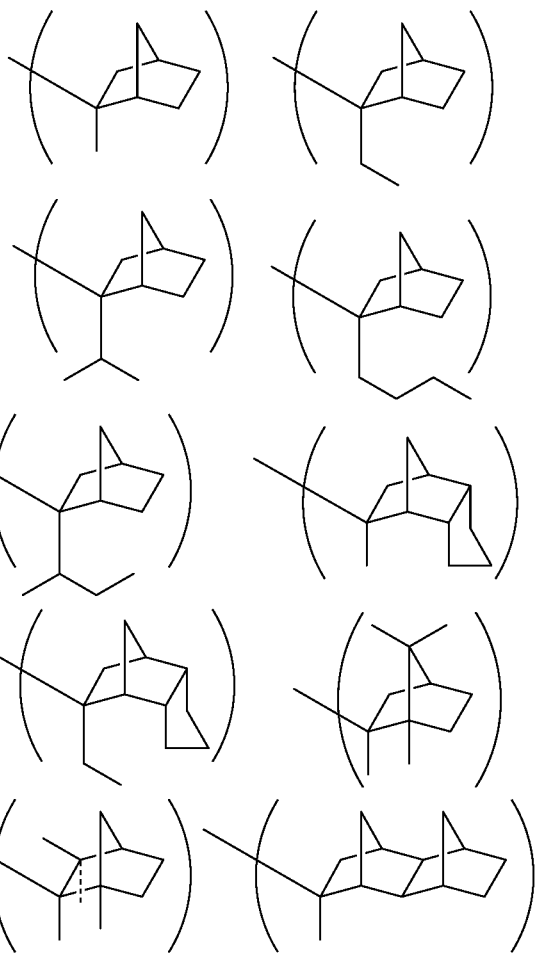

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butyl-cyclopentyl, 1-sec-butylcyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

The acid labile groups of formula (L4) are exemplified by the following groups.

In preparing the polymer of the invention, copolymerization reaction is effected using the lactonecontaining compound of formula (1) as a first monomer and at least one of the compounds of formulae (2) to (10) as a second monomer.

In the copolymerization reaction, the proportions of the respective monomers are properly adjusted so as to produce a polymer which will exert the desired performance when formulated as a resist composition.

If desired, the polymer of the invention is prepared by copolymerizing (i) the first monomer of formula (1) with (ii) at least one second monomer of formulae (2) to (10) and further with (iii) a third monomer having a carbon-to-carbon double bond (other than the first and second monomers). Examples of the third monomer include substituted acrylic esters such as methyl methacrylate, methyl crotonate, dimethyl maleate and dimethyl itaconate, unsaturated carboxylic acids such as maleic acid, fumaric acid and itaconic acid, norbornene and substituted norbornenes such as norbornene-5-methyl carboxylate, unsaturated acid anhydrides such as itaconic anhydride, and other monomers.

The polymers of the invention may contain
(I) from more than 0 mol % to 100 mol %, preferably 1 to 70 mol %, and more preferably 5 to 50 mol % of units of formula (1a-1) or (1a-2) derived from the monomer of formula (1),
(II) from 0 mol % to less than 100 mol %, preferably 1 to 95 mol %, and more preferably 5 to 90 mol % of units of at least one of formulae (2a) to (10a) derived from the monomers of formulae (2) to (10), and (III) 0 to 80 mol %, preferably 0 to 70 mol %, and more preferably 0 to 50 mol % of units derived from at least one of the third monomers.

The polymers of the invention have a weight average molecular weight of about 1,000 to about 500,000, and preferably about 3,000 to about 100,000. Outside the range, there would occur an outstanding decline of etching resistance and a drop of resolution due to a loss of the difference in dissolution rate before and after exposure.

In the third aspect, the invention provides a method for preparing the polymer comprising effecting radical or anionic polymerization between the lactone-containing compound of formula (1) and another compound having a carbon-to-carbon double bond which is the second monomer (ii) and/or third monomer (iii) described above.

For radical polymerization, reaction is preferably carried out in a solvent, for example, hydrocarbons such as benzene, ethers such as tetrahydrofuran, alcohols such as ethanol, or ketones such as methyl isobutyl ketone, using a polymerization initiator, for example, azo compounds such as 2,2'-azobisisobutyronitrile or peroxides such as benzoyl peroxide and lauroyl peroxide. The preferred reaction temperature is from about 0° C. to about 100° C. The preferred reaction time is from about ½ to about 48 hours. Outside these preferred ranges, the reaction may be carried out as well.

For anionic polymerization, reaction is preferably carried out in a solvent, for example, hydrocarbons such as benzene, ethers such as tetrahydrofuran or liquid ammonia, using a polymerization initiator, for example, metals such as sodium and potassium, alkyl metals such as n-butyllithium and sec-butyllithium, ketyl or Grignard reactants. The preferred reaction temperature is from about −78° C. to about 0° C. The preferred reaction time is from about ½ to about 48 hours. Further preferably, a stopper is added, for example, proton donative compounds such as methanol, halides such as methyl iodide or electrophilic agents. Outside these preferred ranges, the reaction may be carried out as well.

Resist composition

Since the polymer of the invention is useful as the base polymer of a resist composition, the fourth aspect of the invention provides a resist composition comprising the polymer. Specifically, the resist composition is defined as comprising the polymer, a compound capable of generating an acid upon exposure to high energy radiation or electron beams, and an organic solvent.

Photoacid generator

The compound capable of generating an acid upon exposure to high energy radiation or electron beams is generally known as a photoacid generator. The photoacid generator used herein includes the following:

(i) onium salts of the formula (P1a-1), (P1a-2) or (P1b),
(ii) diazomethane derivatives of the formula (P2),
(iii) glyoxime derivatives of the formula (P3),
(iv) bissulfone derivatives of the formula (P4),
(v) sulfonic acid esters of N-hydroxyimide compounds of the formula (P5),
(vi) β-ketosulfonic acid derivatives,
(vii) disulfone derivatives,
(viii) nitrobenzylsulfonate derivatives, and
(ix) sulfonate derivatives.

These photoacid generators are described in detail.

(i) Onium salts of formula (P1a-1), (P1a-2) or (P1b)

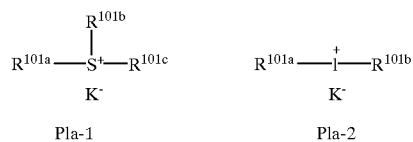

Herein $R^{101a}$, $R^{101b}$ and $R^{101c}$ independently represent straight, branched or cyclic alkyl, alkenyl, oxoalkyl or oxoalkenyl groups of 1 to 12 carbon atoms, aryl groups of 6 to 20 carbon atoms, or aralkyl or aryloxoalkyl groups of 7 to 12 carbon atoms, wherein some or all of the hydrogen atoms may be replaced by alkoxy or other groups. Also, $R^{101b}$ and $R^{101c}$, taken together, may form a ring. $R^{101b}$ and $R^{101c}$ each are alkylene groups of 1 to 6 carbon atoms when they form a ring. $K^-$ is a non-nucleophilic counter ion.

$R^{101a}$, $R^{101b}$, and $R^{101c}$ may be the same or different and are illustrated below. Exemplary alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methyl-cyclohexyl, cyclohexylmethyl, norbornyl, and adamantyl. Exemplary alkenyl groups include vinyl, allyl, propenyl, butenyl, hexenyl, and cyclohexenyl. Exemplary oxoalkyl groups include 2-oxocyclopentyl and 2-oxocyclohexyl as well as 2-oxopropyl, 2-cyclopentyl-2-oxoethyl, 2-cyclohexyl-2-oxoethyl, and 2-(4-methylcyclohexyl)-2-oxoethyl. Exemplary aryl groups include phenyl and naphthyl; alkoxyphenyl groups such as p-methoxyphenyl, m-methoxyphenyl, o-methoxyphenyl, ethoxyphenyl, p-tert-butoxyphenyl, and m-tert-butoxyphenyl; alkylphenyl groups such as 2-methylphenyl, 3-methylphenyl, 4-methylphenyl, ethylphenyl, 4-tert-butylphenyl, 4-butylphenyl, and dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Exemplary aralkyl groups include benzyl, phenylethyl, and phenethyl. Exemplary aryloxoalkyl groups are 2-aryl-2-oxoethyl groups such as 2-phenyl-2-oxoethyl, 2-(1-naphthyl)-2-oxoethyl, and 2-(2-naphthyl)-2-oxoethyl. Examples of the non-nucleophilic counter ion represented by $K^-$ include halide ions such as chloride and bromide ions, fluoroalkylsulfonate ions such as triflate, 1,1,1-trifluoroethanesulfonate, and nonafluorobutanesulfonate, arylsulfonate ions such as tosylate, benzenesulfonate, 4-fluorobenzenesulfonate, and 1,2,3,4,5-pentafluorobenzenesulfonate, and alkylsulfonate ions such as mesylate and butanesulfonate.

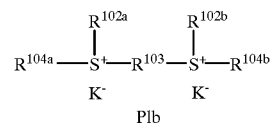

Herein, $R^{102a}$ and $R^{102b}$ independently represent straight, branched or cyclic alkyl groups of 1 to 8 carbon atoms. $R^{103}$ represents a straight, branched or cyclic alkylene groups of 1 to 10 carbon atoms. $R^{104a}$ and $R^{104b}$ independently represent 2-oxoalkyl groups of 3 to 7 carbon atoms. $K^-$ is a non-nucleophilic counter ion.

Illustrative of the groups represented by $R^{102a}$ and $R^{102b}$ are methyl, ethyl, propyl, isopropyl, n-butyl, sec-butyl, tert-butyl, pentyl, hexyl, heptyl, octyl, cyclopentyl, cyclohexyl, cyclopropylmethyl, 4-methylcyclohexyl, and cyclohexylmethyl. Illustrative of the groups represented by $R^{103}$ are methylene, ethylene, propylene, butylene, pentylene, hexylene, heptylene, octylene, nonylene, 1,4-cyclohexylene, 1,2-cyclohexylene, 1,3-cyclopentylene, 1,4-cyclooctylene, and 1,4-cyclohexanedimethylene. Illustrative of the groups represented by $R^{104a}$ and $R^{104b}$ are 2-oxopropyl, 2-oxocyclopentyl, 2-oxocyclohexyl, and 2-oxocycloheptyl. Illustrative examples of the counter ion represented by $K^-$ are the same as exemplified for formulae (P1a-1) and (P1a-2).

(ii) Diazomethane derivatives of formula (P2)

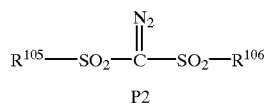

Herein, $R^{105}$ and $R^{106}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms.

Of the groups represented by $R^{105}$ and $R^{106}$, exemplary alkyl groups include methyl, ethyl, propyl, isopropyl, n-butyl, sec-butyl, tert-butyl, pentyl, hexyl, heptyl, octyl, amyl, cyclopentyl, cyclohexyl, cycloheptyl, norbornyl, and adamantyl. Exemplary halogenated alkyl groups include trifluoromethyl, 1,1,1-trifluoroethyl, 1,1,1-trichloroethyl, and nonafluorobutyl. Exemplary aryl groups include phenyl; alkoxyphenyl groups such as p-methoxyphenyl, m-methoxyphenyl, o-methoxyphenyl, ethoxyphenyl, p-tert-butoxyphenyl, and m-tert-butoxyphenyl; and alkylphenyl groups such as 2-methylphenyl, 3-methylphenyl, 4-methylphenyl, ethylphenyl, 4-tert-butylphenyl, 4-butylphenyl, and dimethylphenyl. Exemplary halogenated aryl groups include fluorophenyl, chlorophenyl, and 1,2,3,4,5-pentafluorophenyl. Exemplary aralkyl groups include benzyl and phenethyl.

(iii) Glyoxime derivatives of formula (P3)

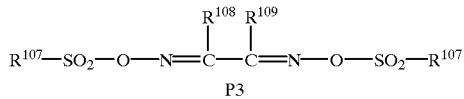

Herein, $R^{107}$, $R^{108}$, and $R^{109}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms. Also, $R^{108}$ and $R^{109}$, taken together, may form a ring. $R^{108}$ and $R^{109}$ each are straight or branched alkylene groups of 1 to 6 carbon atoms when they form a ring.

Illustrative examples of the alkyl, halogenated alkyl, aryl, halogenated aryl, and aralkyl groups represented by $R^{107}$, $R^{108}$, and $R^{109}$ are the same as exemplified for $R^{105}$ and $R^{106}$. Examples of the alkylene groups represented by $R^{108}$ and $R^{109}$ include methylene, ethylene, propylene, butylene, and hexylene.

(iv) Bissulfone derivatives of formula (P4)

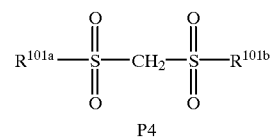

Herein, $R^{101a}$ and $R^{101b}$ are as defined above.

(v) Sulfonic acid esters of N-hydroxyimide compounds of formula (P5)

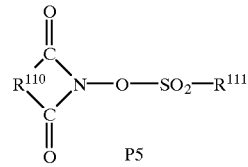

Herein, $R^{110}$ is an arylene group of 6 to 10 carbon atoms, alkylene group of 1 to 6 carbon atoms, or alkenylene group of 2 to 6 carbon atoms wherein some or all of the hydrogen atoms may be replaced by straight or branched alkyl or alkoxy groups of 1 to 4 carbon atoms, nitro, acetyl, or phenyl groups. $R^{111}$ is a straight, branched or cyclic alkyl group of 1 to 8 carbon atoms, alkenyl, alkoxyalkyl, phenyl or naphthyl group wherein some or all of the hydrogen atoms may be replaced by alkyl or alkoxy groups of 1 to 4 carbon atoms, phenyl groups (which may have substituted thereon an alkyl or alkoxy of 1 to 4 carbon atoms, nitro, or acetyl group), hetero-aromatic groups of 3 to 5 carbon atoms, or chlorine or fluorine atoms.

Of the groups represented by $R^{110}$, exemplary arylene groups include 1,2-phenylene and 1,8-naphthylene; exemplary alkylene groups include methylene, 1,2-ethylene, 1,3-propylene, 1,4-butylene, 1-phenyl-1,2-ethylene, and norbornane-2,3-diyl; and exemplary alkenylene groups include 1,2-vinylene, 1-phenyl-1,2-vinylene, and 5-norbornene-2,3-diyl. Of the groups represented by $R^{111}$, exemplary alkyl groups are as exemplified for $R^{101a}$ to $R^{101c}$; exemplary alkenyl groups include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl, and 7-octenyl; and exemplary alkoxyalkyl groups include methoxymethyl, ethoxymethyl, propoxymethyl, butoxymethyl, pentyloxymethyl, hexyloxymethyl, heptyloxymethyl, methoxyethyl, ethoxyethyl, propoxyethyl, butoxyethyl, pentyloxyethyl, hexyloxyethyl, methoxypropyl, ethoxypropyl, propoxypropyl, butoxypropyl, methoxybutyl, ethoxybutyl, propoxybutyl, methoxypentyl, ethoxypentyl, methoxyhexyl, and methoxyheptyl.

Of the substituents on these groups, the alkyl groups of 1 to 4 carbon atoms include methyl, ethyl, propyl, isopropyl, n-butyl, isobutyl and tert-butyl; the alkoxy groups of 1 to 4 carbon atoms include methoxy, ethoxy, propoxy, isopropoxy, n-butoxy, isobutoxy, and tert-butoxy; the phenyl groups which may have substituted thereon an alkyl or alkoxy of 1 to 4 carbon atoms, nitro, or acetyl group include phenyl, tolyl, p-tert-butoxyphenyl, p-acetylphenyl and p-nitrophenyl; the hetero-aromatic groups of 3 to 5 carbon atoms include pyridyl and furyl.

Illustrative examples of the photoacid generator include:
  onium salts such as diphenyliodonium trifluoromethanesulfonate, (p-tert-butoxyphenyl)

phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)-sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclo-hexyl)sulfonium trifluoromethanesulfonate, ethylenebis-[methyl(2-oxocyclopentyl)sulfonium trifluoromethanesulfonate], and 1,2'-naphthylcarbonylmethyltetrahydrothiophenium triflate;

diazomethane derivatives such as bis(benzenesulfonyl)diazomethane, bis(p-toluenesulfonyl)diazomethane, bis(xylenesulfonyl)diazomethane, bis(cyclohexylsulfonyl)-diazomethane, bis(cyclopentylsulfonyl)diazomethane, bis(n-butylsulfonyl)diazomethane, bis(isobutylsulfonyl)-diazomethane, bis(sec-butylsulfonyl)diazomethane, bis(n-propylsulfonyl)diazomethane, bis(isopropylsulfonyl)-diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tert-amylsulfonyl-1-(tert-butylsulfonyl)diazomethane;

glyoxime derivatives such as bis-o-(p-toluenesulfonyl)-α-dimethylglyoxime, bis-o-(p-toluenesulfonyl)-α-diphenylglyoxime, bis-o-(p-toluenesulfonyl)-α-dicyclohexylglyoxime, bis-o-(p-toluenesulfonyl)-2,3-pentanedioneglyoxime, bis-o-(p-toluenesulfonyl)-2-methyl-3,4-pentane-dioneglyoxime, bis-o-(n-butanesulfonyl) -α-dimethylglyoxime, bis-o-(n-butanesulfonyl)-α-diphenylglyoxime, bis-o-(n-butanesulfonyl)-α-dicyclohexylglyoxime, bis-o-(n-butanesulfonyl)-2,3-pentanedioneglyoxime, bis-o-(n-butanesulfonyl)-2-methyl-3,4-pentanedioneglyoxime, bis-o-(methanesulfonyl)-α-dimethylglyoxime, bis-o-(trifluoromethanesulfonyl)-α-dimethylglyoxime, bis-o-(1,1,1-trifluoroethanesulfonyl)-α-dimethylglyoxime, bis-o-(tertbutanesulfonyl)-α-dimethylglyoxime, bis-o-(perfluoro-octanesulfonyl)-α-dimethylglyoxime, bis-o-(cyclohexanesulfonyl)-α-dimethylglyoxime, bis-o-(benzenesulfonyl)-α-dimethylglyoxime, bis-o-(p-fluorobenzenesulfonyl)-α-dimethylglyoxime, bis-o-(p-tert-butylbenzenesulfonyl)-α-dimethylglyoxime, bis-o-(xylenesulfonyl)-α-dimethylglyoxime, and bis-o-(camphorsulfonyl)-α-dimethylglyoxime;

bissulfone derivatives such as bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane;

β-ketosulfone derivatives such as 2-cyclohexylcarbonyl-2-(p-toluenesulfonyl)propane and 2-isopropylcarbonyl-2-(p-toluenesulfonyl)propane;

disulfone derivatives such as diphenyl disulfone and dicyclohexyl disulfone;

nitrobenzyl sulfonate derivatives such as 2,6-dinitrobenzyl p-toluenesulfonate and 2,4-dinitrobenzyl p-toluenesulfonate;

sulfonic acid ester derivatives such as 1,2,3-tris(methanesulfonyloxy)benzene, 1,2,3-tris(trifluoromethanesulfonyloxy)benzene, and 1,2,3-tris(p-toluenesulfonyloxy)benzene; and sulfonic acid esters of N-hydroxyimides such as N-hydroxysuccinimide methanesulfonate, N-hydroxysuccinimide trifluoromethanesulfonate, N-hydroxysuccinimide ethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide 1-octanesulfonate, N-hydroxysuccinimide p-toluenesulfonate, N-hydroxysuccinimide p-methoxybenzenesulfonate, N-hydroxysuccinimide 2-chloroethanesulfonate, N-hydroxysuccinimide benzenesulfonate, N-hydroxysuccinimide 2,4,6-trimethylbenzenesulfonate, N-hydroxysuccinimide 1-naphthalenesulfonate, N-hydroxysuccinimide 2-naphthalenesulfonate, N-hydroxy-2-phenylsuccinimide methanesulfonate, N-hydroxymaleimide methanesulfonate, N-hydroxymaleimide ethanesulfonate, N-hydroxy-2-phenylmaleimide methanesulfonate, N-hydroxyglutarimide methanesulfonate, N-hydroxyglutarimide benzenesulfonate, N-hydroxyphthalimide methanesulfonate, N-hydroxyphthalimide benzenesulfonate, N-hydroxyphthalimide trifluoromethanesulfonate, N-hydroxyphthalimide p-toluenesulfonate, N-hydroxynaphthalimide methanesulfonate, N-hydroxynaphthalimide benzenesulfonate, N-hydroxy-5-norbornene-2,3-dicarboxyimide methanesulfonate, N-hydroxy-5-norbornene-2,3-dicarboxyimide trifluoromethanesulfonate, and N-hydroxy-5-norbornene-2,3-dicarboxyimide p-toluenesulfonate.

Preferred among these photoacid generators are onium salts such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2- oxocyclohexyl)sulfonium trifluoromethanesulfonate, (2-norbornyl)methyl(2-oxocylohexyl)-sulfonium trifluoromethanesulfonate, and 1,2'-naphthylcarbonylmethyltetrahydrothiophenium triflate; diazomethane derivatives such as bis(benzenesulfonyl)-diazomethane, bis(p-toluenesulfonyl)diazomethane, bis (cyclohexylsulfonyl)diazomethane, bis(n-butylsulfonyl)-diazomethane, bis(isobutylsulfonyl)diazomethane, bis(sec-butylsulfonyl)diazomethane, bis(n-propylsulfonyl)-diazomethane, bis(isopropylsulfonyl)diazomethane, and bis (tert-butylsulfonyl)diazomethane; glyoxime derivatives such as bis-o-(p-toluenesulfonyl)-α-dimethylglyoxime and bis-o-(n-butanesulfonyl)-α-dimethylglyoxime; bissulfone derivatives such as bisnaphthylsulfonylmethane; and sulfonic acid esters of N-hydroxyimide compounds such as N-hydroxysuccinimide methanesulfonate, N-hydroxysuccinimide trifluoromethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide p-toluenesulfonate, N-hydroxynaphthalimide methanesulfonate, and N-hydroxynaphthalimide benzenesulfonate.

These photoacid generators may be used singly or in combinations of two or more thereof. Onium salts are effective for improving rectangularity, while diazomethane derivatives and glyoxime derivatives are effective for reducing standing waves. The combination of an onium salt with a diazomethane or a glyoxime derivative allows for fine adjustment of the profile.

The photoacid generator is added in an amount of about 0.1 to 15 parts, and especially about 0.5 to 8 parts by weight, per 100 parts by weight of the base resin (all parts are by weight, hereinafter). Less than 0.1 part of the photoacid generator would provide a poor sensitivity whereas more than 15 parts of the photoacid generator would lower the rate of alkali dissolution to reduce the resolution of resist compositions and also lower the heat resistance because of the excessive presence of lower molecular weight components.

Organic solvent

The organic solvent used herein may be any organic solvent in which the base resin, photoacid generator, and other components are soluble. Illustrative, non-limiting, examples of the organic solvent include ketones such as cyclohexanone and methyl-2-n-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate. These solvents may be used alone or in combinations of two or more thereof. Of the above organic solvents, it is recommended to use diethylene glycol dimethyl ether and 1-ethoxy-2-propanol because the photoacid generator serving as one of the resist components is most soluble therein, propylene glycol monomethyl ether acetate because it is a safe solvent, or a mixture thereof.

An appropriate amount of the organic solvent used is about 200 to 1,000 parts, especially about 400 to 800 parts by weight per 100 parts by weight of the base resin.

To the resist composition of the invention, another polymer other than the polymer of the invention may also be added. The other polymers that can be added to the resist composition are, for example, those polymers comprising lo units of the following formula (R1) or (R2) or both and having a weight average molecular weight of about 1,000 to about 500,000, especially about 5,000 to about 100,000 although the other polymers are not limited thereto.

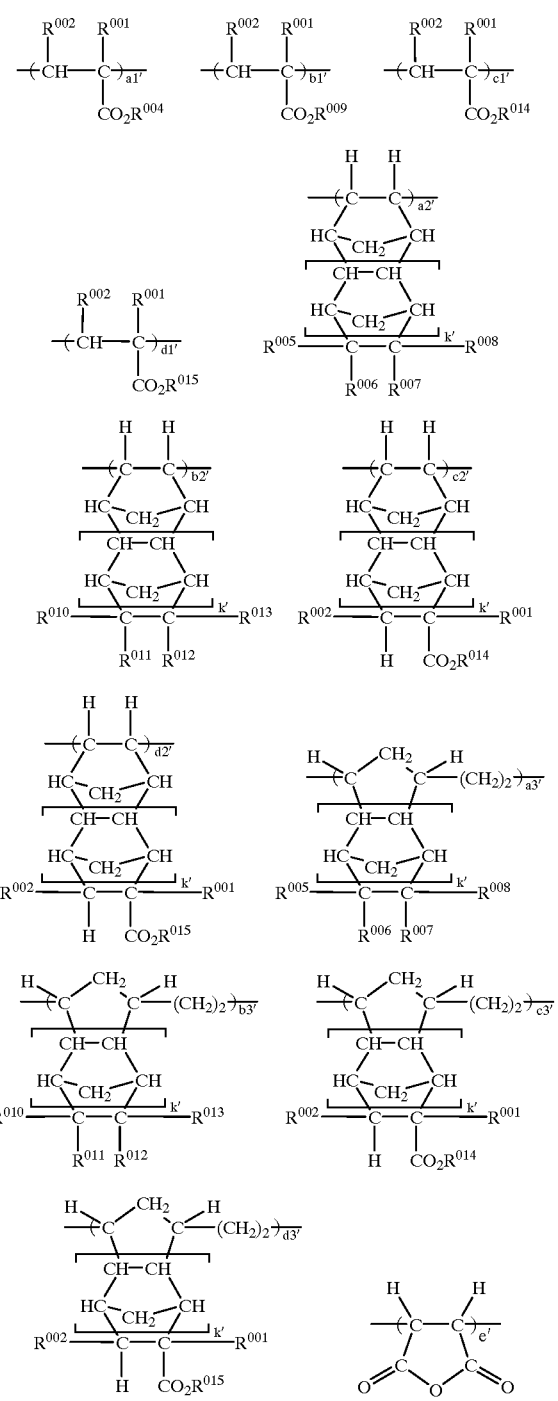

(R1)

-continued

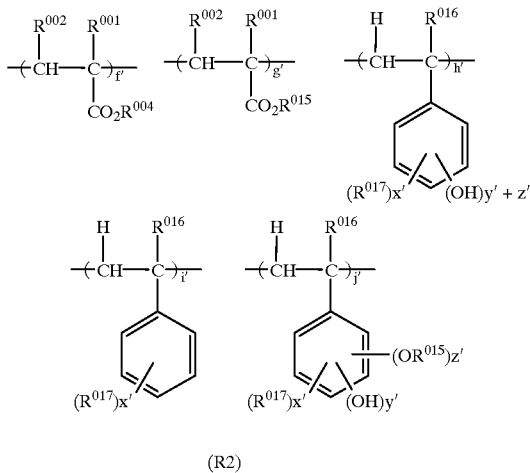

(R2)

Herein, $R^{001}$ is hydrogen, methyl or $CH_2CO_2R^{003}$. $R^{002}$ is hydrogen, methyl or $CO_2R^{003}$. $R^{003}$ is a straight, branched or cyclic alkyl group of 1 to 15 carbon atoms. $R^{004}$ is hydrogen or a monovalent hydrocarbon group of 1 to 15 carbon atoms having a carboxyl or hydroxyl group. At least one of $R^{005}$ to $R^{008}$ represents a monovalent hydrocarbon group of 1 to 15 carbon atoms having a carboxyl or hydroxyl group while the remaining R's independently represent hydrogen or a straight, branched or cyclic alkyl group of 1 to 15 carbon atoms. Alternatively, $R^{005}$ to $R^{008}$, taken together, may form a ring, and in that event, at least one of $R^{005}$ to $R^{008}$ is a divalent hydrocarbon group of 1 to 15 carbon atoms having a carboxyl or hydroxyl group, while the remaining R's are independently single bonds or straight, branched or cyclic alkylene groups of 1 to 15 carbon atoms. $R^{009}$ is a monovalent hydrocarbon group of 3 to 15 carbon atoms containing a —$CO_2$— partial structure. At least one of $R^{010}$ to $R^{013}$ is a monovalent hydrocarbon group of 2 to 15 carbon atoms containing a —$CO_2$— partial structure, while the remaining R's are independently single bonds or hydrogen or straight, branched or cyclic alkyl groups of 1 to 15 carbon atoms. $R^{010}$ to $R^{013}$, taken together, may form a ring, and in that event, at least one of $R^{010}$ to $R^{013}$ is a divalent hydrocarbon group of 1 to 15 carbon atoms containing a —$CO_2$— partial structure, while the remaining R's are independently straight, branched or cyclic alkylene groups of 1 to 15 carbon atoms. $R^{014}$ is a polycyclic hydrocarbon group having 7 to 15 carbon atoms or an alkyl group containing a polycyclic hydrocarbon group. $R^{015}$ is an acid labile group. $R^{016}$ is hydrogen or methyl. $R^{017}$ is a straight, branched or cyclic alkyl group of 1 to 8 carbon atoms. Letter k' is equal to 0 or 1; a1', a2', a3', b1', b2', b3', c1', c2', c3', d1', d2', d3', and e' are numbers from 0 to less than 1, satisfying a1'+a2'+a3'+b1+b2'+b3'+c1'+c2'+c3'+d1'+d2'+d3'+e'=1; f', g', h', i', and j' are numbers from 0 to less than 1, satisfying f'+g'+h'+i'+j'=1. Illustrative examples of the respective groups are the same as exemplified for $R^1$ to $R^{17}$.

The inventive polymer and the other polymer are preferably blended in a weight ratio from 10:90 to 90:10, more preferably from 20:80 to 80:20. If the blend ratio of the inventive polymer is below this range, the resist composition would become poor in some of the desired properties. The properties of the resist composition can be adjusted by properly changing the blend ratio of the inventive polymer.

The polymer is not limited to one type and a mixture of two or more other polymers may be added. The use of plural polymers allows for easy adjustment of resist properties.

Dissolution inhibitor

To the resist composition, a dissolution inhibitor may be added. The dissolution inhibitor is a compound having on the molecule at least two phenolic hydroxyl groups, in which an average of from 0 to 100 mol % of all the hydrogen atoms on the phenolic hydroxyl groups are replaced with acid labile groups or a compound having on the molecule at least one carboxyl group, in which an average of 80 to 100 mol % of all the hydrogen atoms on the carboxyl groups are replaced with acid labile groups, both the compounds having an average molecular weight within a range of 100 to 1,000, and preferably 150 to 800.

The degree of substitution of the hydrogen atoms on the phenolic hydroxyl groups or carboxyl groups with acid labile groups is on average at least 0 mol %, and preferably at least 30 mol %, of all the phenolic hydroxyl groups or carboxyl groups. The upper limit is 100 mol %, and preferably 80 mol %.

Preferable examples of such compounds having two or more phenolic hydroxyl groups or compounds having a carboxyl group include those of formulas (D1) to (D14) below.

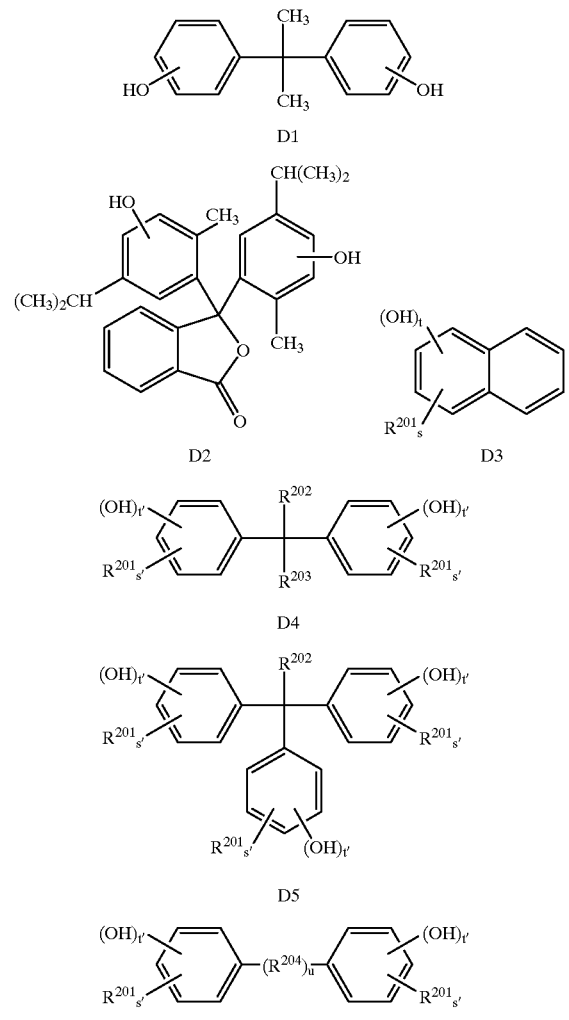

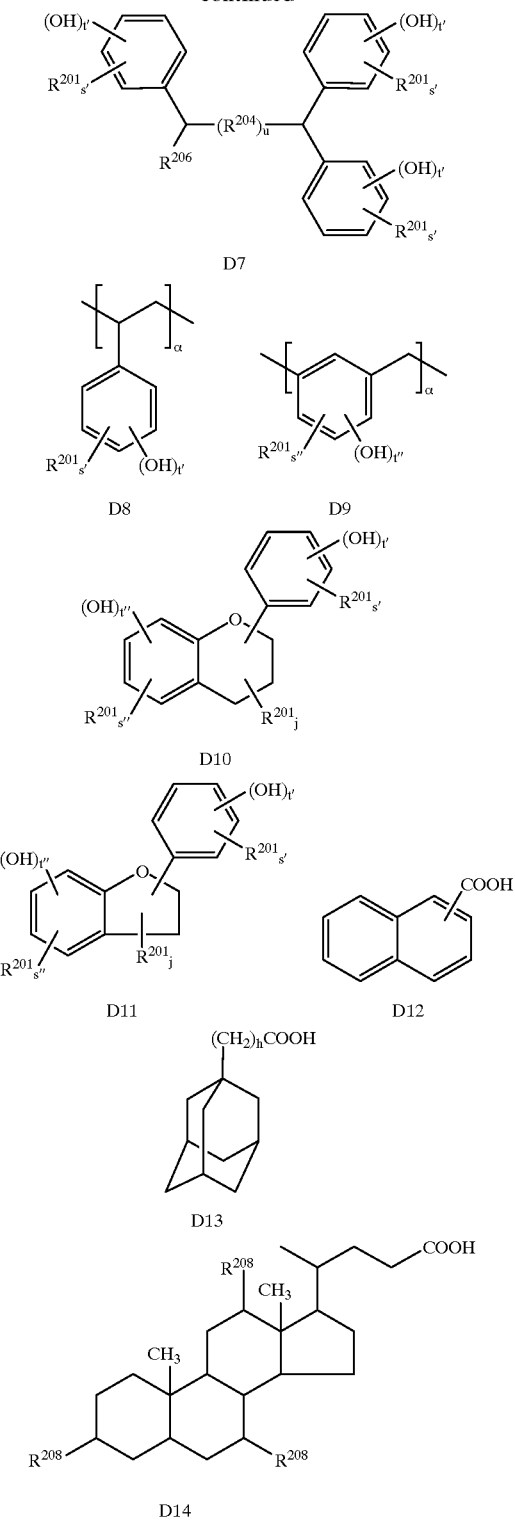

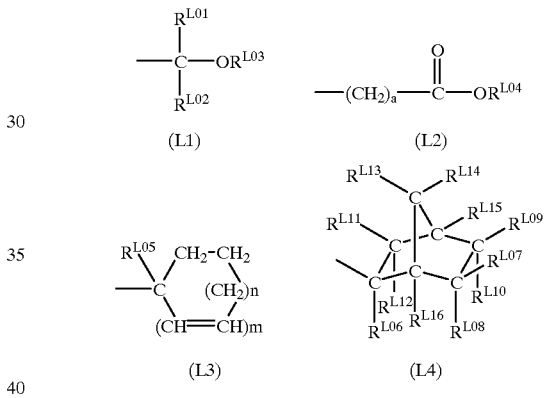

In these formulas, $R^{201}$ and $R^{202}$ are each hydrogen or a straight or branched alkyl or alkenyl of 1 to 8 carbon atoms; $R^{203}$ is hydrogen, a straight or branched alkyl or alkenyl of 1 to 8 carbon atoms, or —$(R^{207})_h$—COOH; $R^{204}$ is —($CH_2$)$_i$— (where i=2 to 10), an arylene of 6 to 10 carbon atoms, carbonyl, sulfonyl, an oxygen atom, or a sulfur atom; $R^{205}$ is an alkylene of 1 to 10 carbon atoms, an arylene of 6 to 10 carbon atoms, carbonyl, sulfonyl, an oxygen atom, or a sulfur atom; $R^{206}$ is hydrogen, a straight or branched alkyl or alkenyl of 1 to 8 carbon atoms, or a hydroxyl-substituted phenyl or naphthyl; $R^{207}$ is a straight or branched alkylene of 1 to 10 carbon atoms; $R^{208}$ is hydrogen or hydroxyl; the letter ; is an integer from 0 to 5; u and h are each 0 or 1; s, t, s', t', s", and t" are each numbers which satisfy s+t=8, s'+t'=5, and s"+t"=4, and are such that each phenyl skeleton has at least one hydroxyl group; and a is α number such that the molecular weight of the compounds of formula (D8) or (D9) is from 100 to 1,000.

In the above formulas, suitable examples of $R^{201}$ and $R^{202}$ include hydrogen, methyl, ethyl, butyl, propyl, ethynyl, and cyclohexyl; suitable examples of $R^{203}$ include the same groups as for $R^{201}$ and $R^{202}$, as well as —COOH and —$CH_2$COOH; suitable examples of $R^{204}$ include ethylene, phenylene, carbonyl, sulfonyl, oxygen, and sulfur; suitable examples of $R^{205}$ include methylene as well as the same groups as for $R^{204}$; and suitable examples of $R^{206}$ include hydrogen, methyl, ethyl, butyl, propyl, ethynyl, cyclohexyl, and hydroxylsubstituted phenyl or naphthyl.

Exemplary acid labile groups on the dissolution inhibitor include groups of the following general formulae (L1) to (L4), tertiary alkyl groups of 4 to 20 carbon atoms, trialkylsilyl groups in which each of the alkyls has 1 to 6 carbon atoms, and oxoalkyl groups of 4 to 20 carbon atoms.

In these formulas, $R^{L01}$ to $R^{L16a}$, m and n are as defined and exemplified above.

The dissolution inhibitor may be formulated in an amount of 0 to 50 parts, preferably 5 to 50 parts, and more preferably 10 to 30 parts, per 100 parts of the base resin, and may be used singly or as a mixture of two or more thereof. Less than 5 parts of the dissolution inhibitor may fail to yield an improved resolution, whereas the use of more than 50 parts would lead to thinning of the patterned film, and thus a decline in resolution.

The dissolution inhibitor can be synthesized by introducing acid labile groups into a compound having phenolic hydroxyl or carboxyl groups in accordance with an organic chemical formulation.

Basic compound

In the resist composition of the invention, a basic compound may be blended. A suitable basic compound used herein is a compound capable of suppressing the rate of diffusion when the acid generated by the photoacid generator diffuses within the resist film. The inclusion of this type of basic compound holds down the rate of acid diffusion within the resist film, resulting in better resolution. In addition, it suppresses changes in sensitivity following exposure, thus reducing substrate and environment dependence, as well as improving the exposure latitude and the pattern profile.

Examples of basic compounds include primary, secondary, and tertiary aliphatic amines, mixed amines, aromatic amines, heterocyclic amines, carboxyl group-bearing nitrogenous compounds, sulfonyl group-bearing nitrogenous compounds, hydroxyl group-bearing nitrogenous compounds, hydroxyphenyl group-bearing nitrogenous compounds, alcoholic nitrogenous compounds, amide derivatives, and imide derivatives.

Examples of suitable primary aliphatic amines include ammonia, methylamine, ethylamine, n-propylamine, isopropylamine, n-butylamine, iso-butylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, di-iso-propylamine, di-n-butylamine, di-iso-butylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, tri-iso-propylamine, tri-n-butylamine, tri-iso-butylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable carboxyl group-bearing nitrogenous compounds include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of suitable sulfonyl group-bearing nitrogenous compounds include 3-pyridinesulfonic acid and pyridinium p-toluenesulfonate. Examples of suitable hydroxyl group-bearing nitrogenous compounds, hydroxyphenyl group-bearing nitrogenous compounds, and alcoholic nitrogenous compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]-piperazine, piperidine ethanol, 1-(2-hydroxyethyl)-pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)-isonicotinamide. Examples of suitable amide derivatives include formamide, N-methylformamide, N,N-dimethylformamide, acetamide, N-methylacetamide, N,N-dimethylacetamide, propionamide, and benzamide. Suitable imide derivatives include phthalimide, succinimide, and maleimide.

In addition, basic compounds of the following general formulas (B1) and (B2) may also be included.

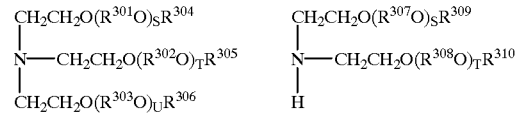

B1            B2

In the formulas, $R^{301}$, $R^{302}$, $R^{303}$, $R^{307}$ and $R^{308}$ are independently straight, branched or cyclic alkylenes of 1 to 20 carbon atoms; $R^{304}$, $R^{305}$, $R^{306}$, $R^{309}$ and $R^{310}$ are hydrogen, alkyls of 1 to 20 carbon atoms, or amino; $R^{304}$ and $R^{305}$, $R^{304}$ and $R^{306}$, $R^{305}$ and $R^{307}$, $R^{304}$ with $R^{305}$ and $R^{306}$ and $R^{309}$ and $R^{310}$ may bond together to form rings; and S, T and U are each integers from 0 to 20, with the proviso that hydrogen is excluded from $R^{304}$, $R^{305}$, $R^{306}$, $R^{309}$ and $R^{310}$ when S, T and U are equal to 0.

The alkylene groups represented by $R^{301}$, $R^{302}$, $R^{303}$, $R^{307}$ and $R^{308}$ preferably have 1 to 20 carbon atoms, more preferably 1 to 10 carbon atoms, and most preferably 1 to 8 carbon atoms. Examples include methylene, ethylene, n-propylene, isopropylene, n-butylene, isobutylene, n-pentylene, isopentylene, hexylene, nonylene, decylene, cyclopentylene, and cyclohexylene.

The alkyl groups represented by $R^{304}$, $R^{305}$, $R^{306}$, $R^{309}$ and $R^{310}$ preferably have 1 to 20 carbon atoms, more preferably 1 to 8 carbon atoms, and most preferably 1 to 6 carbon atoms, and may be straight, branched or cyclic. Examples include methyl, ethyl, n-propyl, isopropyl, n-butyl, isobutyl, tert-butyl, n-pentyl, isopentyl, hexyl, nonyl, decyl, dodecyl, tridecyl, cyclopentyl, and cyclohexyl.

Where $R^{304}$ and $R^{305}$, $R^{304}$ and $R^{306}$, $R^{305}$ and $R^{306}$, $R^{304}$ with $R^{305}$ and $R^{306}$, and $R^{309}$ and $R^{310}$ form rings, the rings preferably have 1 to 20 carbon atoms, more preferably 1 to 8 carbon atoms, and most preferably 1 to 6 carbon atoms, and may have branching alkyl groups of 1 to 6 carbon atoms, and especially 1 to 4 carbon atoms.

S, T, and U are each integers from 0 to 20, preferably from 1 to 10, and more preferably from 1 to 8.

Illustrative examples of the compounds of formulas (B1) and (B2) include tris{2-(methoxymethoxy)ethyl}amine, tris{2-(methoxyethoxy)ethyl}amine, tris[2-{(2-methoxyethoxy)methoxy}ethyl]amine, tris{2-(2-methoxyethoxy)-ethyl}amine, tris{2-(1-methoxyethoxy) ethyl}amine, tris{2-(1-ethoxyethoxy)ethyl}amine, tris{2-(1-ethoxypropoxy)-ethyl}amine, tris[2-{(2-hydroxyethoxy) ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, and 1-aza-18-crown-6. Especially preferred basic compounds are tertiary amines, 30 aniline derivatives, pyrrolidine derivatives, pyridine derivatives, quinoline derivatives, amino acid derivatives, hydroxyl group-bearing nitrogenous compounds, hydroxyphenyl group-bearing nitrogenous compounds, alcoholic nitrogenous compounds, amide derivatives, imide derivatives, tris{2-(methoxymethoxy)ethyl}amine, tris{2-(2-methoxyethoxy)-ethyl}amine, tris[2-{(2-methoxyethoxy)methyl}ethyl] amine, and 1-aza-15-crown-5.

The basic compound is preferably formulated in an amount of about 0.001 to 10 parts, and especially about 0.01 to 1 part, per part of the photoacid generator. Less than 0.001 part of the basic compound fails to achieve the desired effects thereof, while the use of more than 10 parts would result in too low a sensitivity and resolution.

Other components

In the resist composition, a compound bearing a ≡C—COOH group in a molecule may be blended. Exemplary, non-limiting compounds bearing a ≡C—COOH group include one or more compounds selected from Groups I and II below. Including this compound improves the PED stability of the resist and ameliorates edge roughness on nitride film substrates. Group I:

Compounds in which some or all of the hydrogen atoms on the phenolic hydroxyl groups of the compounds of general formulas (A1) to (A10) below are replaced with —$R^{401}$—COOH (wherein $R^{401}$ is a straight or branched alkylene of 1 to 10 carbon atoms), and in which the molar ratio C/(C+D) of phenolic hydroxyl groups (C) to ≡C—COOH groups (D) in the molecule is from 0.1 to 1.0.

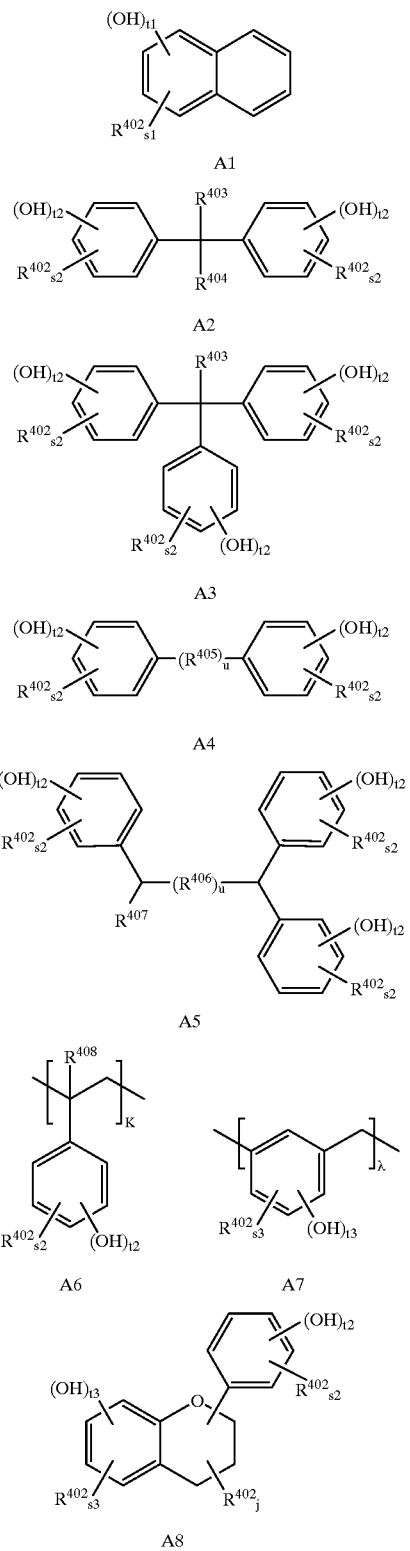

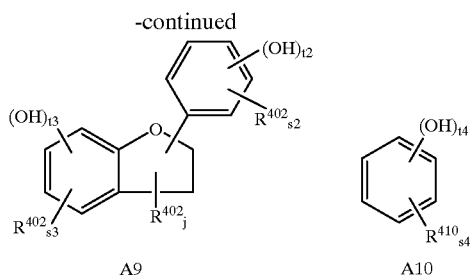

In these formulas, $R^{408}$ is hydrogen or methyl; $R^{402}$ and $R^{403}$ are each hydrogen or a straight or branched alkyl or alkenyl of 1 to 8 carbon atoms; $R^{404}$ is hydrogen, a straight or branched alkyl or alkenyl of 1 to 8 carbon atoms, or a —$(R^{409})_n$—COOR' group (R' being hydrogen or —$R^{409}$—COOH); $R^{405}$ is —$(CH_2)_i$— (wherein i is 2 to 10), an arylene of 6 to 10 carbon atoms, carbonyl, sulfonyl, an oxygen atom, or a sulfur atom; $R^{406}$ is an alkylene of 1 to 10 carbon atoms, an arylene of 6 to 10 carbon atoms, carbonyl, sulfonyl, an oxygen atom, or a sulfur atom; $R^{407}$ is hydrogen, a straight or branched alkyl or alkenyl of 1 to 8 carbon atoms, or a hydroxyl-substituted phenyl or naphthyl; $R^{409}$ is a straight or branched alkylene of 1 to 10 carbon atoms; $R^{410}$ is hydrogen, a straight or branched alkyl or alkenyl of 1 to 8 carbon atoms, or a —$R^{411}$-COOH group; $R^{411}$ is a straight or branched alkylene of 1 to 10 carbon atoms; the letter ; is an integer from 0 to 5; u and h are each 0 or 1; s1, t1, s2, t2, s3, t3, s4, and t4 are each numbers which satisfy s1+t1=8, s2+t2=5, s3+t3=4, and s4+t4=6, and are suc each phenyl skeleton has at least one hydroxyl group; κ is a number such that the compound of formula (A6) may have a weight average molecular weight of 1,000 to 5,000; and λ is a number such that the compound of formula (A7) may have a weight average molecular weight of 1,000 to 10,000.

Group II:
Compounds of general formulas (A11) to (A15) below.

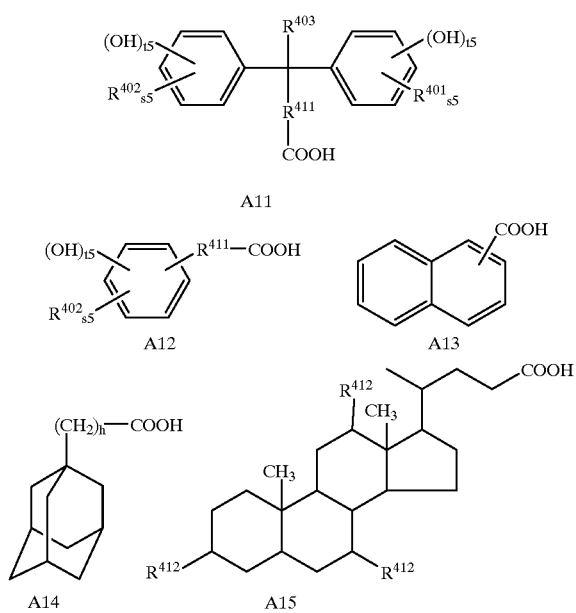

In these formulas, $R^{402}$, $R^{403}$, and $R^{411}$ are as defined above; $R^{412}$ is hydrogen or hydroxyl; s5 and t5 are numbers which satisfy s5≧0, t5≧0, and s5+t5=5; and h' is equal to 0 or 1.

Illustrative, non-limiting examples of the compound bearing a ≡C—COOH group include compounds of the general formulas AI-1 to AI-14 and AII-1 to AII-10 below.

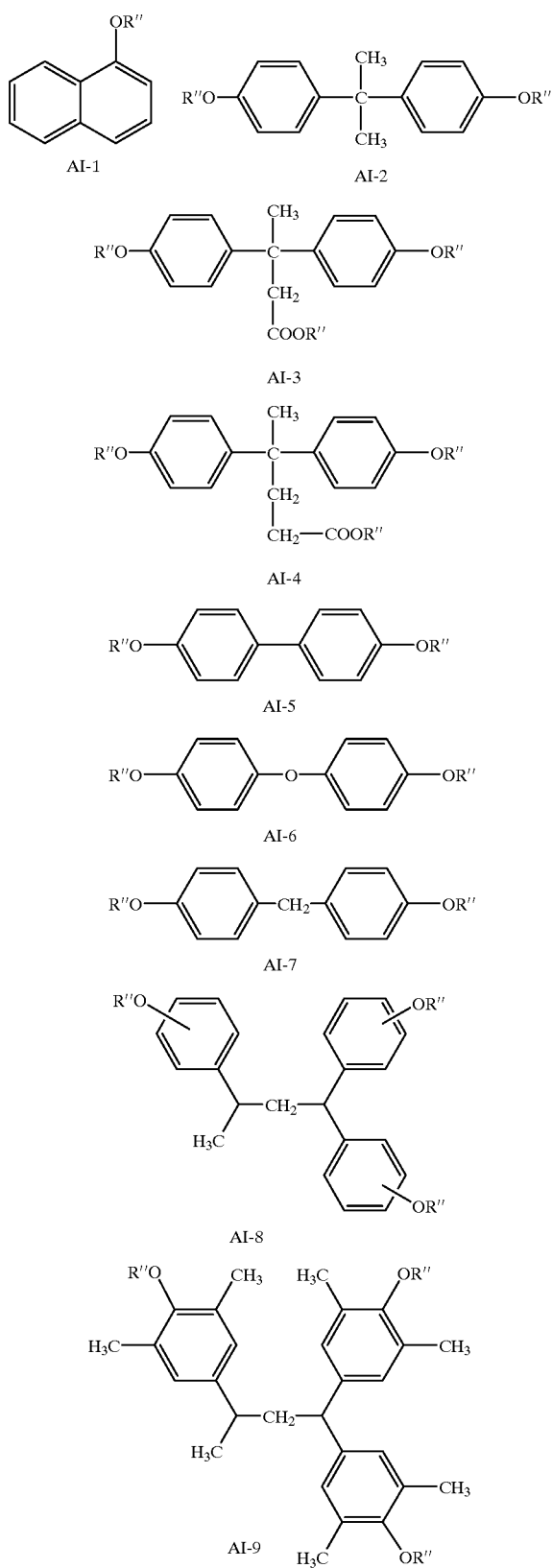

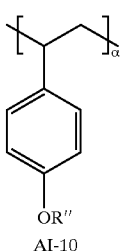
AI-10

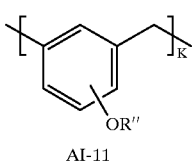
AI-11

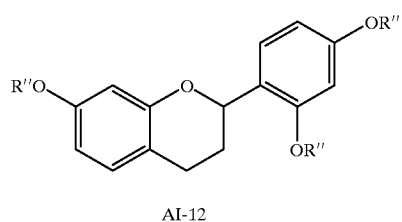
AI-12

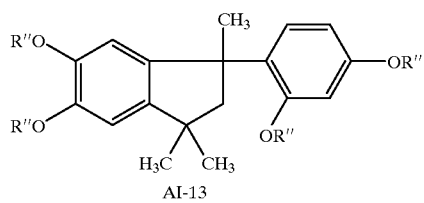
AI-13

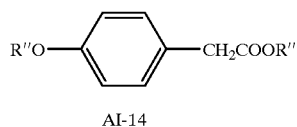
AI-14

In the above formulas, R" is hydrogen or a CH₂COOH group such that the CH₂COOH group accounts for 10 to 100 mol % of R" in each compound, α and κ are as defined above.

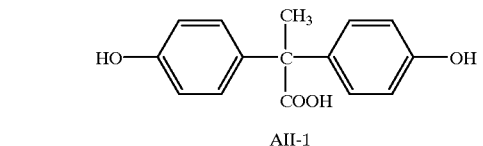
AII-1

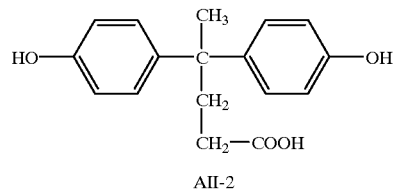
AII-2

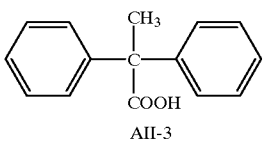
AII-3

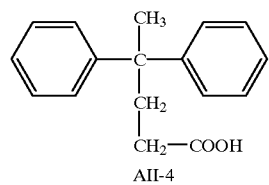
AII-4

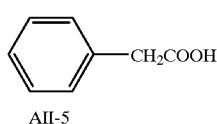
AII-5

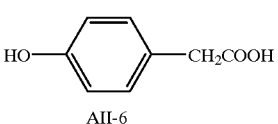
AII-6

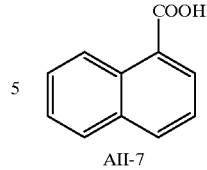
AII-7

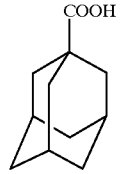
AII-8

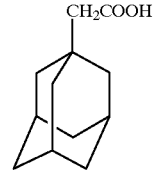
AII-9

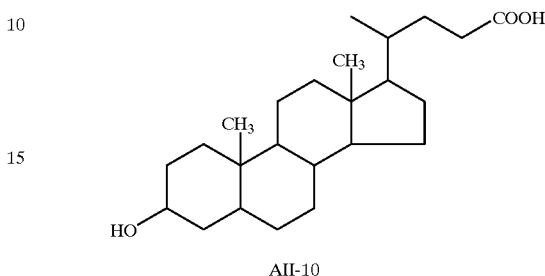
AII-10

The compound bearing a ≡C—COOH group within the molecule may be used singly or as combinations of two or more thereof.

The compound bearing a ≡C—COOH group within the molecule is added in an amount ranging from about 0 to 5 parts, preferably about 0.1 to 5 parts, more preferably about 0.1 to 3 parts, and further preferably about 0.1 to 2 parts, per 100 parts of the base resin. More than 5 parts of the compound can reduce the resolution of the resist composition.

The resist composition of the invention may additionally include an acetylene alcohol derivative for the purpose of enhancing the shelf stability. Preferred acetylene alcohol derivaatives are those having the general formula (S1) or (S1) below.

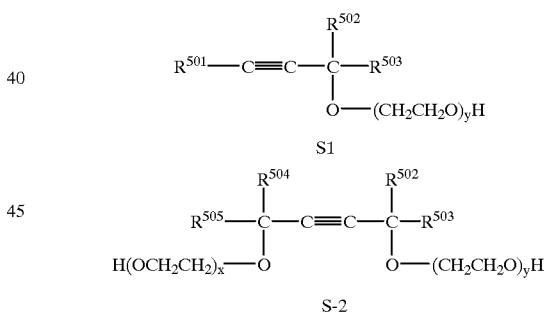

In the formulas, $R^{501}$, $R^{502}$, $R^{503}$, $R^{504}$, and $R^{505}$ are each hydrogen or a straight, branched, or cyclic alkyl of 1 to 8 carbon atoms; and X and Y are each 0 or a positive number, satisfying $0 \leq X \leq 30$, $0 \leq Y \leq 30$, and $0 \leq X+Y \leq 40$.

Preferable examples of the acetylene alcohol derivative include Surfynol 61, Surfynol 82, Surfynol 104, Surfynol 104E, Surfynol 104H, Surfynol 104A, Surfynol TG, Surfynol PC, Surfynol 440, Surfynol 465, and Surfynol 485 from Air Products and Chemicals Inc., and Surfynol E1004 from Nisshin Chemical Industry K.K.

The acetylene alcohol derivative is preferably added in an amount of 0.01 to 2% by weight, and more preferably 0.02 to 1% by weight, per 100% by weight of the resist composition. Less than 0.01% by weight would be ineffective for improving coating characteristics and shelf stability, whereas more than 2% by weight would result in a resist having a low resolution.

The resist composition of the invention may include, as an optional ingredient, a surfactant which is commonly used for improving the coating characteristics. Optional ingredients may be added in conventional amounts so long as this does not compromise the objects of the invention.

Nonionic surfactants are preferred, examples of which include perfluoroalkylpolyoxyethylene ethanols, fluorinated alkyl esters, perfluoroalkylamine oxides, perfluoroalkyl EO-addition products, and fluorinated organosiloxane compounds. Useful surfactants are commercially available under the trade names Florade FC-430 and FC-431 from Sumitomo 3M K.K., Surflon S-141 and S-145 from Asahi Glass K.K., Unidine DS-401, DS-403 and DS-451 from Daikin Industry K.K., Megaface F-8151 from Dai-Nippon Ink & Chemicals K.K., and X-70-092 and X-70-093 from Shin-Etsu Chemical Co., Ltd. Preferred surfactants are Florade FC-430 from Sumitomo 3M K.K. and X-70-093 from Shin-Etsu Chemical Co., Ltd.

Pattern formation using the resist composition of the invention may be carried out by a known lithographic technique. For example, the resist composition is applied onto a substrate such as a silicon wafer by spin coating or the like to form a resist film having a thickness of 0.3 to 2.0 µm, which is then pre-baked on a hot plate at 60 to 150° C. for 1 to 10 minutes, and preferably at 80 to 120° C. for 1 to 5 minutes. A patterning mask having the desired pattern is then placed over the resist film, and the film exposed through the mask to an electron beam or to high-energy radiation such as deep-UV rays, an excimer laser, or x-rays in a dose of about 1 to 200 mJ/cm$^2$, and preferably about 10 to 100 mJ/cm$^2$, then post-exposure baked (PEB) on a hot plate at 60 to 150° C. for 1 to 5 minutes, and preferably at 80 to 130° C. for 1 to 3 minutes. Finally, development is carried out using as the developer an aqueous alkali solution, such as a 0.1 to 5% (preferably 2 to 3%) aqueous solution of tetramethylammonium hydroxide (TMAH), this being done by a conventional method such as dipping, puddling, or spraying for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV rays having a wavelength of 193 to 248 nm, an excimer laser, x-rays, or an electron beam. The desired pattern may not be obtainable outside the upper and lower limits of the above range.

The resist composition comprising the polymer of the invention as a base resin lends itself to micropatterning with electron beams or deep-UV rays since it is sensitive to high-energy radiation and has excellent sensitivity, resolution, and etching resistance. Especially because of the minimized absorption at the exposure wavelength of an ArF or KrF excimer laser, a finely defined pattern having sidewalls perpendicular to the substrate can easily be formed.

EXAMPLE

Examples of the invention are given below by way of illustration and not by way of limitation.

First described are examples of synthesizing lactonecontaining compounds according to the invention and examples of preparing polymers therefrom.

Synthetic Example 1-1
Synthesis of Monomer 1

In 300 ml of benzene was dissolved 324.3 g of acrylic acid. Below 40° C., 327.2 g of cyclopentadiene was added dropwise to the solution over 2 hours. After agitation was continued for 12 hours at room temperature, the reaction mixture was concentrated in vacuum, yielding 608.5 g of 5-norbornene-2-carboxylic acid. The yield was 97.9%.

With 328.2 g of 5-norbornene-2-carboxylic acid was mixed 240.6 of formic acid. Below 50° C., 254.5 g of 35% aqueous hydrogen peroxide was added dropwise to the mixture over 6 hours. After the completion of addition, the reaction mixture was poured into a mixture of 1.5 liters of water and 0.8 kg of sodium sulfite. After three times of extraction with 1 liter of ethyl acetate, the organic phase was washed with water, dried, and concentrated in vacuum. The residue was dissolved in 1.2 liters of methanol, to which a catalytic amount of potassium carbonate was added. This was agitated for one hour at room temperature. The methanol was distilled off under vacuum, followed by conventional extraction and washing. There was obtained 247.6 g of 2-hydroxy-4-oxatricyclo[4.2.1.0$^{3,7}$]nonan-5-one. The yield was 65.5%.

In 1 liter of methylene chloride were dissolved 231.2 g of 2-hydroxy-4-oxatricyclo[4.2.1.0$^{3,7}$]nonan-5-one and 227.2 g of triethylamine. To this mixture below 15° C., 188.2 g of methacrylic chloride was added dropwise over one hour. After the completion of addition, the solution was agitated for 2 hours at room temperature, followed by conventional extraction and washing. The oily substance collected was purified by silica gel column chromatography, yielding 236.8 g of methacrylic acid 5-oxo-4-oxatricyclo[4.2.1.0$^{3,7}$]nonan-2-yl, designated Monomer 1. The yield was 71.0%.

$^1$H-NMR (CDCl$_3$, 270 MHz): δ 1.64 (1H, ddd), 1.77 (1H, ddd), 1.92 (3H, d), 1.96–2.11 (2H, m), 2.52–2.61 (2H, m), 3.21 (1H, ddd), 4.55 (1H, d), 4.62 (1H, d), 5.59 (1H, t), 6.08 (1H, t) FT-IR (NaCl): 1776 cm$^{-1}$, 1712 cm$^{-1}$, 1635 cm$^{-1}$ Synthetic Examples 1-2
Synthesis of Monomer 2

Monomer 2 was synthesized by the same procedure as in the synthesis of Monomer 1 except that dimethyl maleate was used instead of acrylic acid.

$^1$H-NMR (CDCl$_3$, 270 MHz): δ 1.80 (1H, ddd), 1.93 (3H, s), 1.96 (1H, ddd), 2.78 (1H, s), 2.91 (1H, s), 3.09 (1H, d), 3.24 (1H, d), 3.09 (3H, s), 4.59 (1H, d), 4.66 (1H, d), 5.61 (1H, t), 6.09 (1H, t) FT-IR (NaCl): 1797 cm$^{-1}$, 1734 cm$^{-1}$, 1714 cm$^{-1}$, 1633 cm$^{-1}$ Synthetic Examples 1-3 to 1-8
Synthesis of Monomers 3 to 8

Monomers 3 to 8 were similarly synthesized.

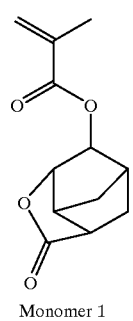

Monomer 1

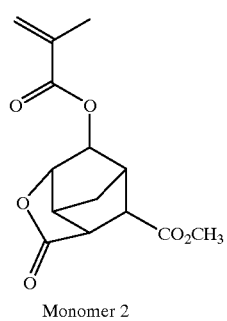

Monomer 2

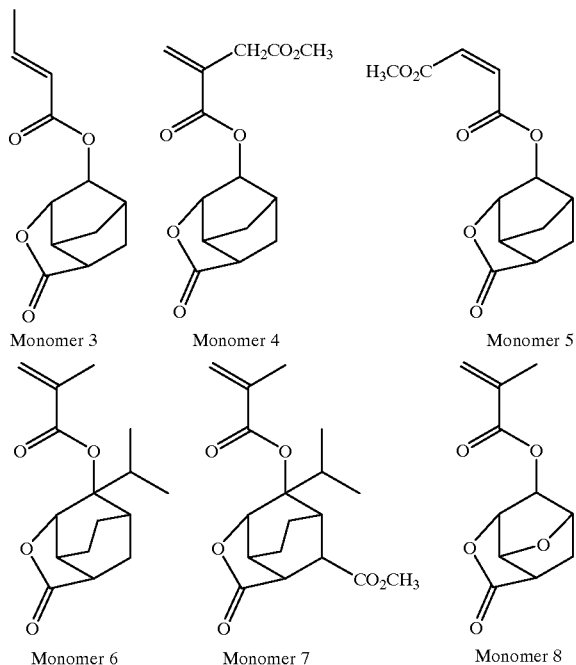

Synthetic Example 2-1
Synthesis of Polymer 1

In 2 liters of tetrahydrofuran, 88.8 g of Monomer 1, 8.6 g of 3-carboxy-1-methylpropyl methacrylate and 78.1 g of tert-butyl methacrylate were dissolved, and 13.1 g of 2,2'-azobisisobutyronitrile added. After agitation was continued for 15 hours at 60° C., the reaction solution was concentrated in vacuum. The residue was dissolved in 800 ml of tetrahydrofuran and added dropwise to 20 liters of n-hexane. The resulting solids were collected by filtration, washed with 20 liters of n-hexane, and dried in vacuum at 40° C. for 6 hours, obtaining 101.2 g of a polymer, designated Polymer 1. The yield was 57.6%.

Synthetic Example 2-2
Synthesis of Polymer 2

In 2 liters of tetrahydrofuran, 112.0 g of Monomer 2, 8.6 g of 3-carboxy-1-methylpropyl methacrylate and 78.1 g of tert-butyl methacrylate were dissolved, and 13.1 g of 2,2'-azobisisobutyronitrile added. After agitation was continued for 15 hours at 60° C., the reaction solution was concentrated in vacuum. The residue was dissolved in 800 ml of tetrahydrofuran and added dropwise to 20 liters of n-hexane. The resulting solids were collected by filtration, washed with 20 liters of n-hexane, and dried in vacuum at 40° C. for 6 hours, obtaining 106.8 g of a polymer, designated Polymer 2. The yield was 53.7%.

Synthetic Examples 2-3 to 2-40
Synthesis of Polymers 3 to 40

Polymers 3 to 40 were similarly synthesized.

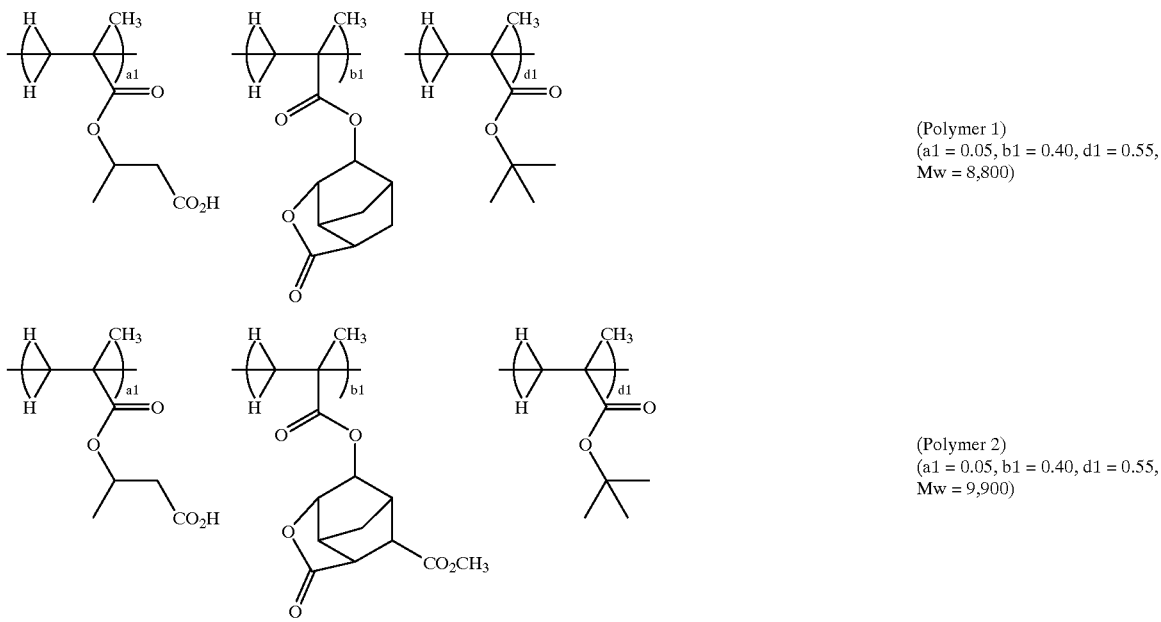

(Polymer 1)
(a1 = 0.05, b1 = 0.40, d1 = 0.55, Mw = 8,800)

(Polymer 2)
(a1 = 0.05, b1 = 0.40, d1 = 0.55, Mw = 9,900)

-continued
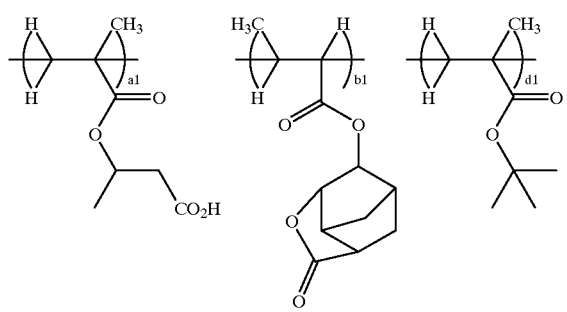
(Polymer 3)
(a1 = 0.05, b1 = 0.40, d1 = 0.55, Mw = 9,100)
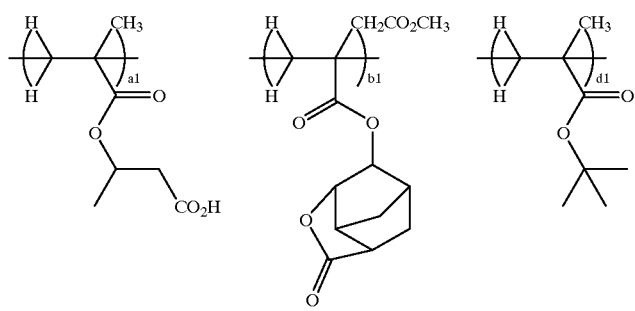
(Polymer 4)
(a1 = 0.05, b1 = 0.40, d1 = 0.55, Mw = 9,900)
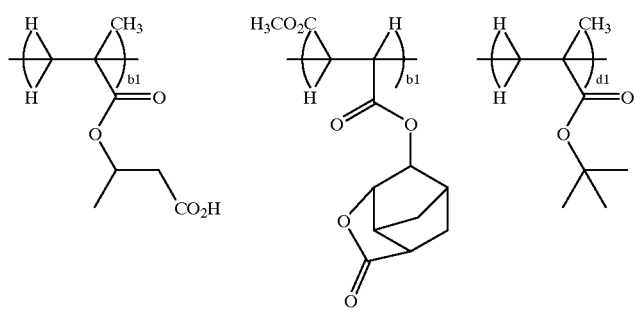
(Polymer 5)
(a1 = 0.05, b1 = 0.40, d1 = 0.55, Mw = 9,900)
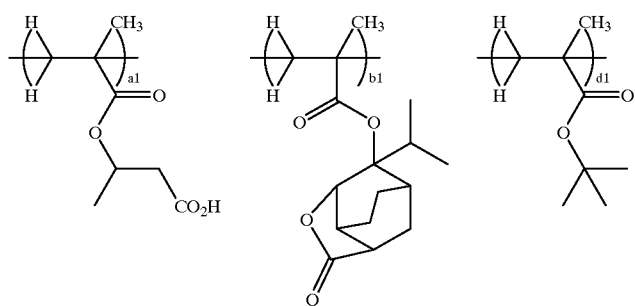
(Polymer 6)
(a1 = 0.05, b1 = 0.40, d1 = 0.55, Mw = 9,900)
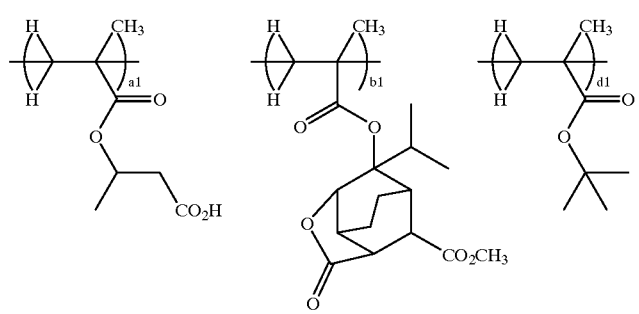
(Polymer 7)
(a1 = 0.05, b1 = 0.40, d1 = 0.55, Mw = 11,100)

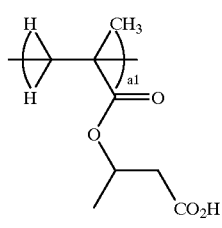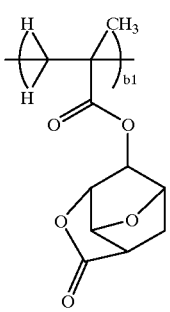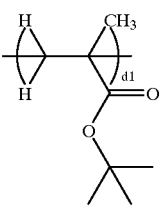
(Polymer 8)
(a1 = 0.05, b1 = 0.40, d1 = 0.55, Mw = 8,800)
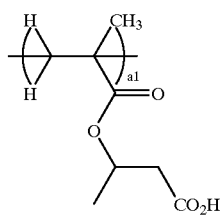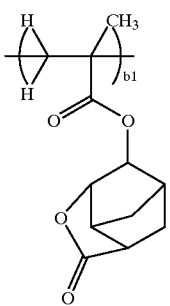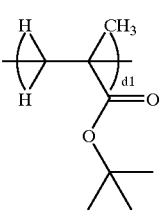
(Polymer 9)
(a1 = 0.10, b1 = 0.20, d1 = 0.70, Mw = 8,100)
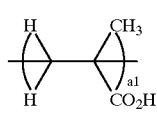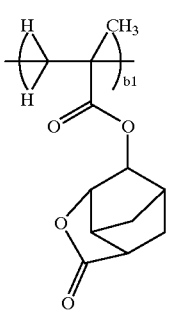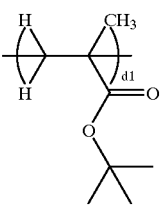
(Polymer 10)
(a1 = 0.10, b1 = 0.20, d1 = 0.70, Mw = 7,600)
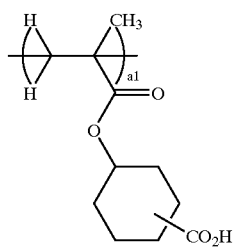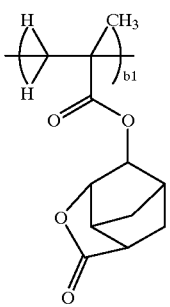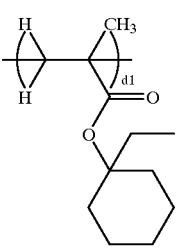
(Polymer 11)
(a1 = 0.10, b1 = 0.20, d1 = 0.70, Mw = 8,300)
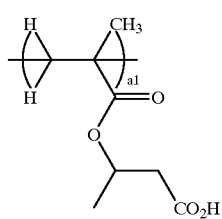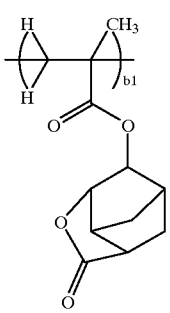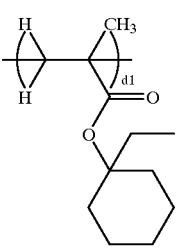
(Polymer 12)
(a1 = 0.10, b1 = 0.20, d1 = 0.70, Mw = 10,000)

-continued
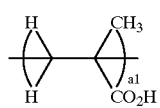 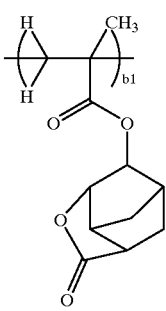 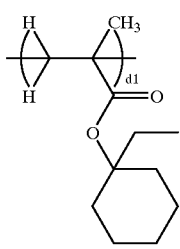
(Polymer 13)
(a1 = 0.10, b1 = 0.20, d1 = 0.70, Mw = 9,500)
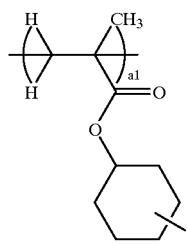 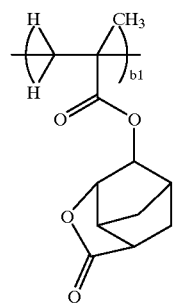 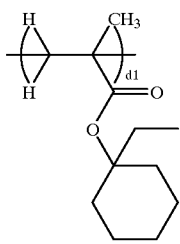
(Polymer 14)
(a1 = 0.10, b1 = 0.20, d1 = 0.70, Mw = 10,200)
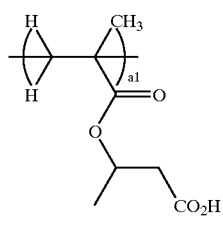 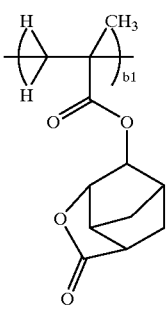 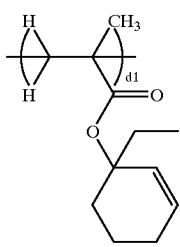
(Polymer 15)
(a1 = 0.10, b1 = 0.20, d1 = 0.70, Mw = 9,900)
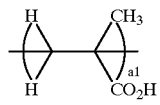 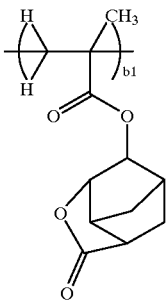 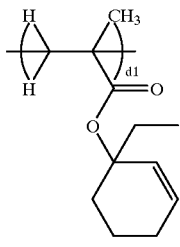
(Polymer 16)
(a1 = 0.10, b1 = 0.20, d1 = 0.70, Mw = 9,500)
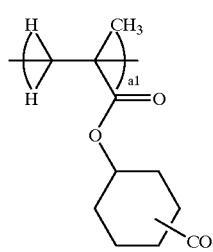 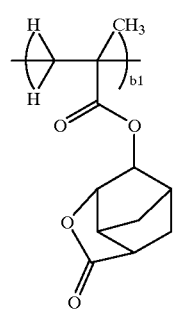 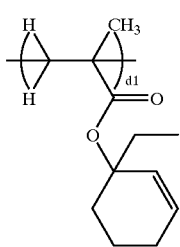
(Polymer 17)
(a1 = 0.10, b1 = 0.20, d1 = 0.70, Mw = 10,100)

-continued
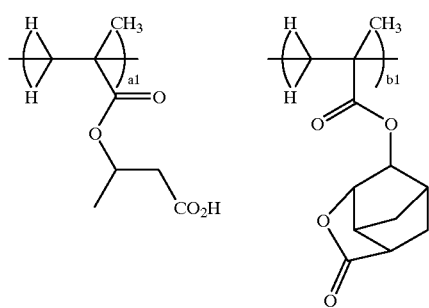
(Polymer 18)
(a1 = 0.10, b1 = 0.20, d1 = 0.70,
Mw = 9,500)
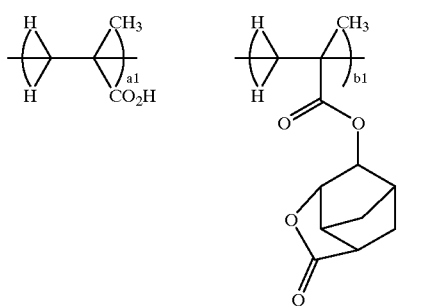
(Polymer 19)
(a1 = 0.10, b1 = 0.20, d1 = 0.70,
Mw = 9,000)
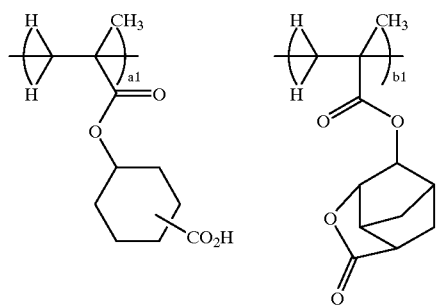
(Polymer 20)
(a1 = 0.10, b1 = 0.20, d1 = 0.70,
Mw = 9,700)
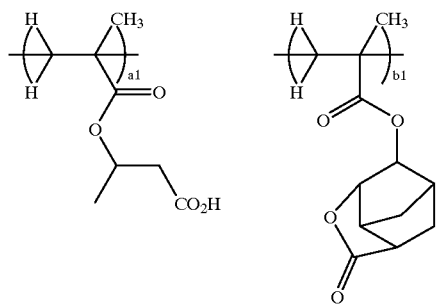
(Polymer 21)
(a1 = 0.10, b1 = 0.40, d1 = 0.50,
Mw = 19,200)
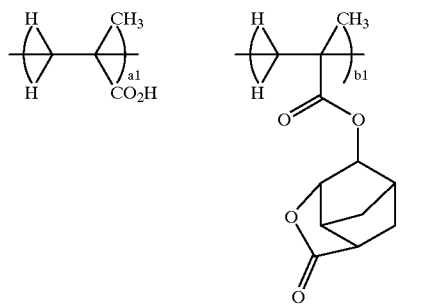
(Polymer 22)
(a1 = 0.10, b1 = 0.40, d1 = 0.50,
Mw = 18,200)

-continued
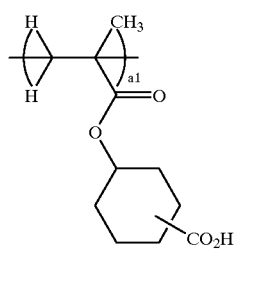 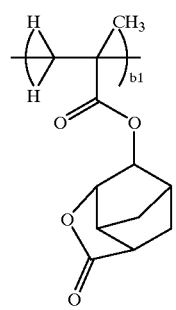 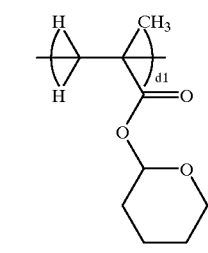
(Polymer 23)
(a1 = 0.10, b1 = 0.40, d1 = 0.50, Mw = 19,600)
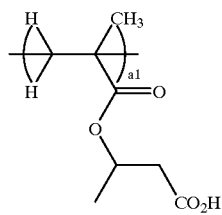 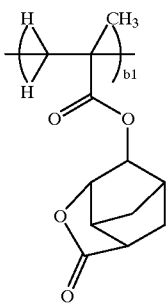 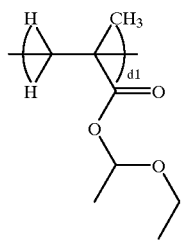
(Polymer 24)
(a1 = 0.10, b1 = 0.40, d1 = 0.50, Mw = 18,600)
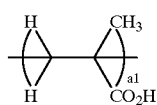 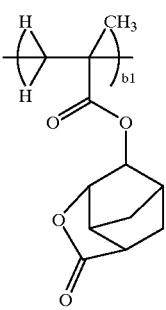 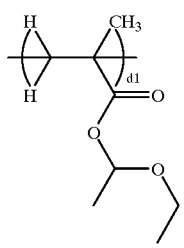
(Polymer 25)
(a1 = 0.10, b1 = 0.40, d1 = 0.50, Mw = 17,600)
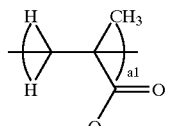 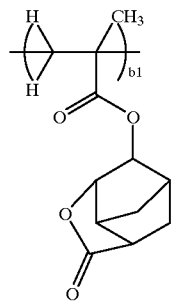 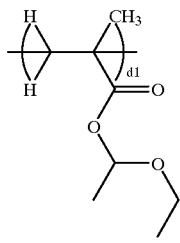
(Polymer 26)
(a1 = 0.10, b1 = 0.40, d1 = 0.50, Mw = 19,000)
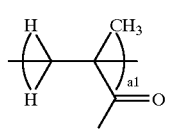 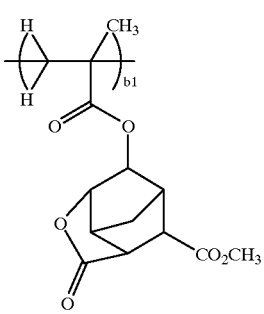 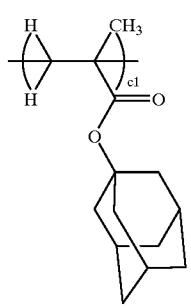 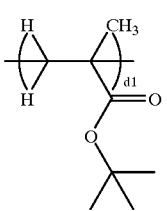
(Polymer 27)
(a1 = 0.05, b1 = 0.25, c1 = 0.30, d1 = 0.40, Mw = 15,200)

-continued
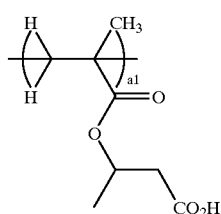 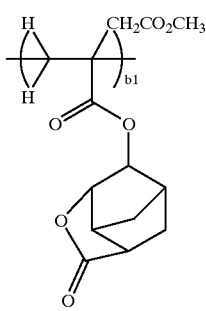 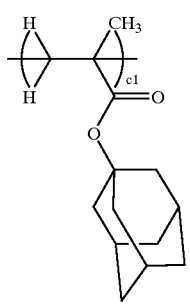 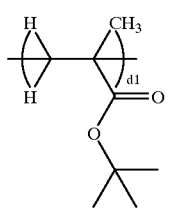
(Polymer 28)
(a1 = 0.05, b1 = 0.25, c1 = 0.30, d1 = 0.40, Mw = 15,200)
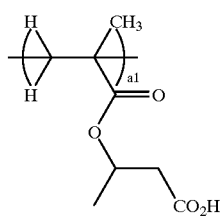 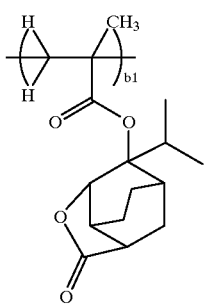 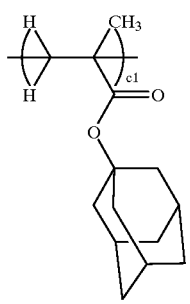 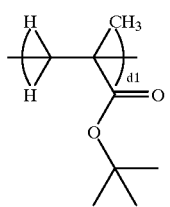
(Polymer 29)
(a1 = 0.05, b1 = 0.25, c1 = 0.30, d1 = 0.40, Mw = 15,200)
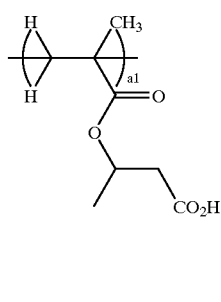 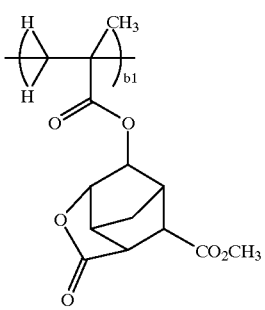 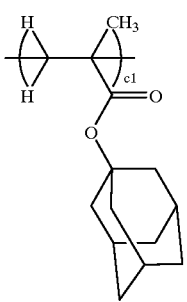 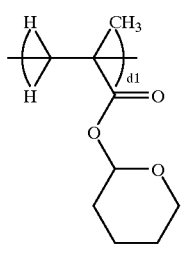
(Polymer 30)
(a1 = 0.05, b1 = 0.25, c1 = 0.30, d1 = 0.40, Mw = 15,900)
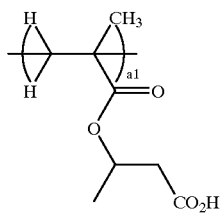 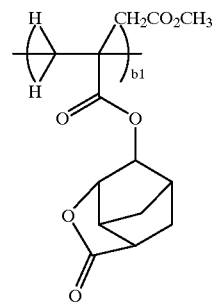 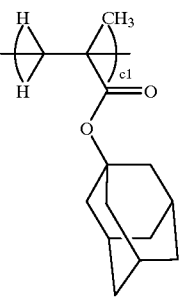 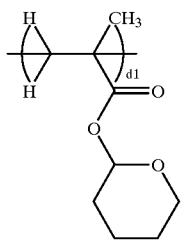
(Polymer 31)
(a1 = 0.05, b1 = 0.25, c1 = 0.30, d1 = 0.40, Mw = 15,900)
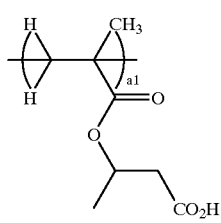 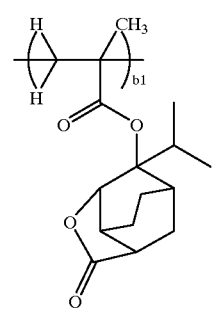 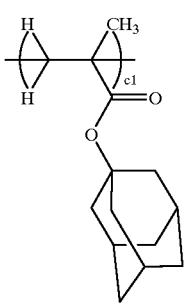 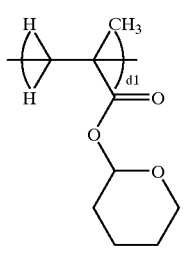
(Polymer 32)
(a1 = 0.05, b1 = 0.25, c1 = 0.30, d1 = 0.40, Mw = 15,900)

-continued
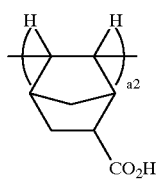 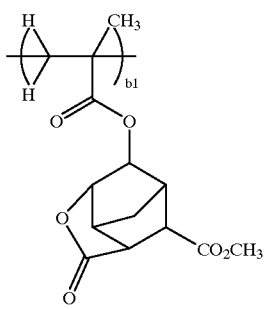 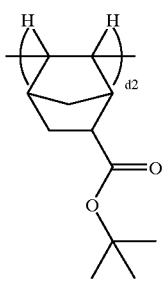 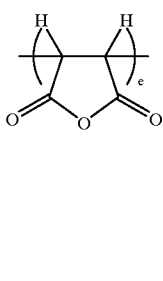
(Polymer 33)
(a2 = 0.05, b1 = 0.10, d2 = 0.40, e = 0.45, Mw = 7,800)
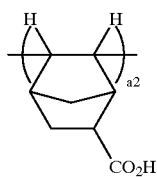 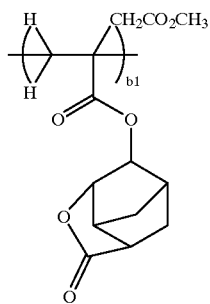 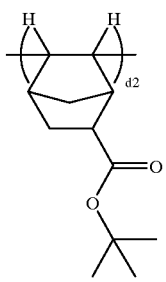 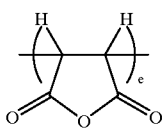
(Polymer 34)
(a2 = 0.05, b1 = 0.10, d2 = 0.40, e = 0.45, Mw = 7,800)
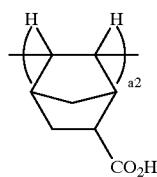 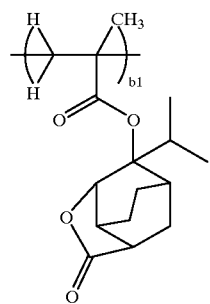 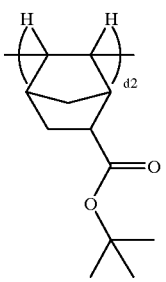 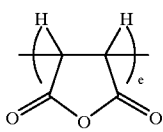
(Polymer 35)
(a2 = 0.05, b1 = 0.10, d2 = 0.40, e = 0.45, Mw = 7,800)
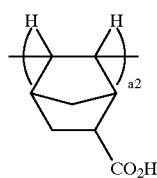 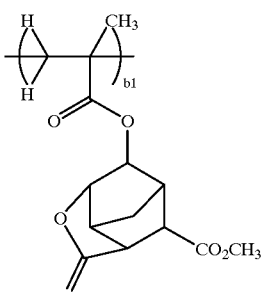 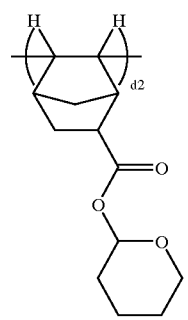 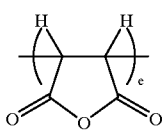
(Polymer 36)
(a2 = 0.05, b1 = 0.10, d2 = 0.40, e = 0.45, Mw = 8,400)
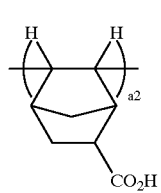 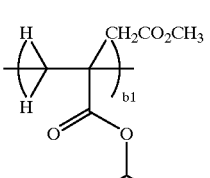 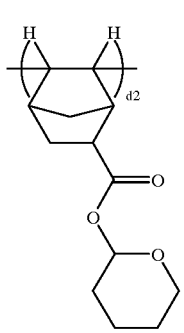 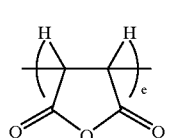
(Polymer 37)
(a2 = 0.05, b1 = 0.10, d2 = 0.40, e = 0.45, Mw = 8,400)

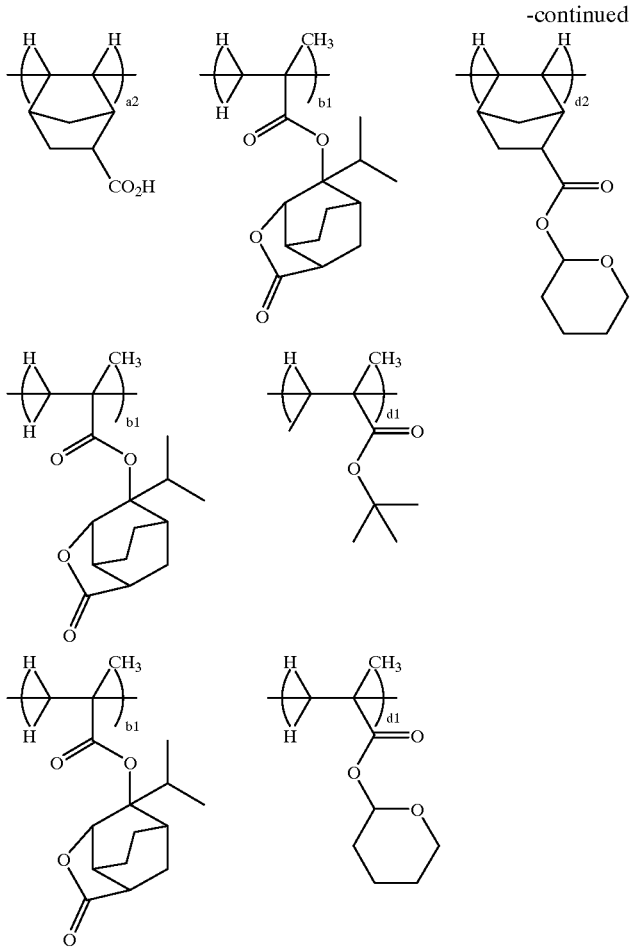

(Polymer 38)
(a2 = 0.05, b1 = 0.10, d2 = 0.40,
e = 0.45, Mw = 8,400)

(Polymer 39)
(b1 = 0.50, d1 = 0.50,
Mw = 31,500)

(Polymer 40)
(b1 = 0.50, d1 = 0.50,
Mw = 33,600)

Examples I-1 to T-70

Evaluation of resist resolution

Resist compositions were formulated using Polymers 1 to 40 obtained in the above Synthetic Examples and examined for resolution.

Resist compositions were prepared by using Polymers 1 to 40 or Polymers 41 to 42 shown below as a base resin, and dissolving the polymer, a photoacid generator (designated as PAG 1 to 8), a dissolution inhibitor (designated as DRR 1 to 4), a basic compound, and a compound having a ≡C—COOH group in the molecule (ACC 1) in a solvent containing 0.05% by weight of surfactant Florade FC-430 (Sumitomo 3M) in the combination shown in Tables 1 to 3. These compositions were each filtered through a 0.2 μm Teflon® filter, thereby giving resist solutions.

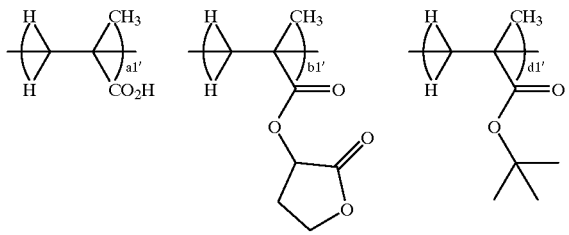

(Polymer 41)
(a1' = 0.15, b1' = 0.35, d1 = 0.50,
Mw = 8,900)

-continued
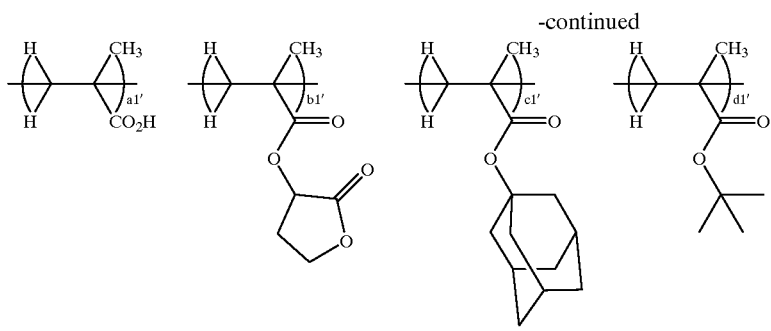
(Polymer 42)
(a1' = 0.15, b1' = 0.20, c1' = 0.15, d1' = 0.50, Mw = 10,200)
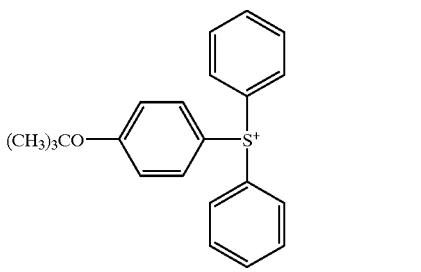  (PAG 1)
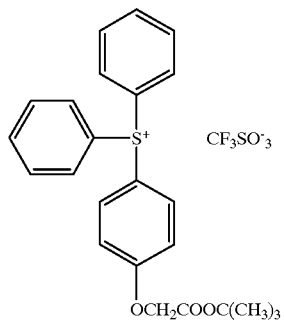 (PAG 2)
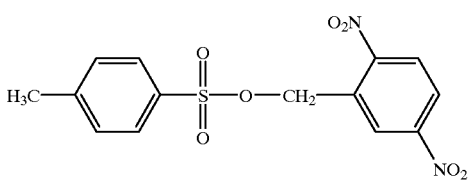 (PAG 3)
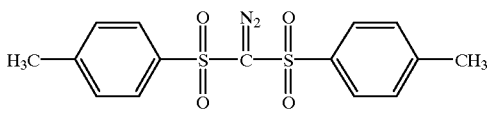 (PAG 4)
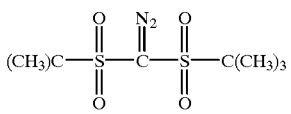 (PAG 5)
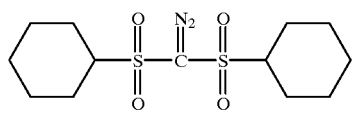 (PAG 6)
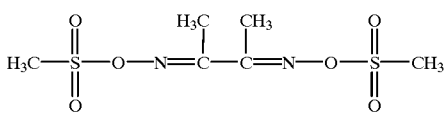 (PAG 7)
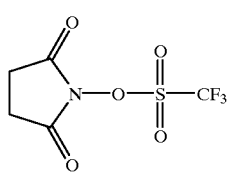 (PAG 8)

-continued

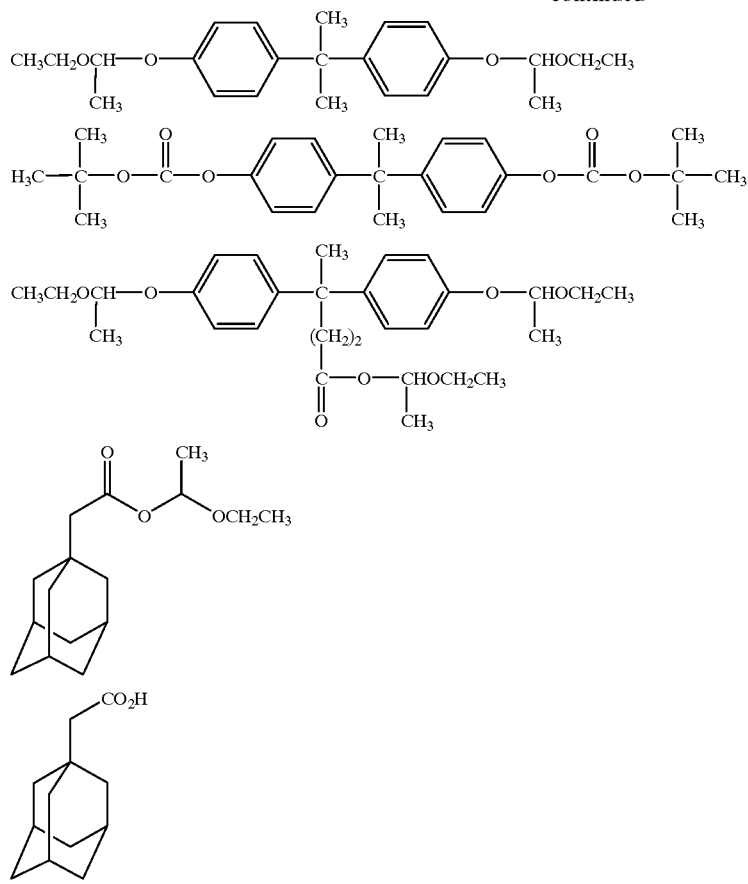

(DRR 1)

(DRR 2)

(DRR 3)

(DRR 4)

(ACC 1)

The solvents and basic compounds used are as follows.
PGMEA: propylene glycol methyl ether acetate
PG/EL: a mixture of 70% PGMEA and 30% ethyl lactate
TBA: tributylamine
TEA: triethanolamine
TMMEA: trismethoxymethoxyethylamine
TMEMEA: trismethoxyethoxymethoxyethylamine These resist solutions were spin-coated onto silicon wafers, then baked at 110° C. for 90 seconds on a hot plate to give resist films having a thickness of 0.5 μm. The resist films were exposed using an ArF excimer laser stepper (Nikon Corporation; NA 0.55), then baked (PED) at 110° C. for 90 seconds, and developed with a solution of 2.38% tetramethylammonium hydroxide in water, thereby giving positive patterns.

The resulting resist patterns were evaluated as described below. First, the sensitivity (Eth, $mJ/cm^2$) was determined. Next, the optimal dose (sensitivity Eop, $mJ/cm^2$) was defined as the dose which provides a 1:1 resolution at the top and bottom of a 0.25 μm line-and-space pattern, and the resolution of the resist under evaluation was defined as the minimum line width (μm) of the lines and spaces that separated at this dose. The shape of the resolved resist pattern was examined under a scanning electron microscope.

The composition and test results of the resist materials are shown in Tables 1 to 3.

TABLE 1

| Example | Base resin | Photoacid generator | Dissolution inhibitor | Basic compound | Solvent | Sensitivity | Resolution | Shape |
|---------|------------|---------------------|-----------------------|----------------|---------|-------------|------------|-------|
| I-1 | Polymer 1 (80) | PAG 1 (2) | — | TBA (0.125) | PGMEA (600) | 6.5 | 0.18 | rectangular |
| I-2 | Polymer 2 (80) | PAG 1 (2) | — | TBA (0.125) | PGMEA (600) | 6.4 | 0.18 | rectangular |
| I-3 | Polymer 3 (80) | PAG 1 (2) | — | TBA (0.125) | PGMEA (600) | 6.5 | 0.18 | rectangular |
| I-4 | Polymer 4 (80) | PAG 1 (2) | — | TBA (0.125) | PGMEA (600) | 6.3 | 0.20 | rectangular |
| I-5 | Polymer 5 (80) | PAG 1 (2) | — | (TBA) (0.125) | PGMEA (600) | 6.3 | 0.20 | rectangular |
| I-6 | Polymer 6 (80) | PAG 1 (2) | — | TBA (0.125) | PGMEA (600) | 6.1 | 0.18 | rectangular |
| I-7 | Polymer 7 | PAG 1 (2) | — | TBA | PGMEA | 6.0 | 0.18 | rectangular |

TABLE 1-continued

| Example | Base resin | Photoacid generator | Dissolution inhibitor | Basic compound | Solvent | Sensitivity | Resolution | Shape |
|---|---|---|---|---|---|---|---|---|
| | (80) | | | (0.125) | (600) | | | |
| I-8 | Polymer 8 (80) | PAG 1 (2) | — | TBA (0.125) | PGMEA (600) | 6.5 | 0.18 | rectangular |
| I-9 | Polymer 9 (80) | PAG 1 (2) | — | TBA (0.125) | PGMEA (600) | 6.0 | 0.18 | rectengular |
| I-10 | Polymer 10 (80) | PAG 1 (2) | — | TBA (0.125) | PGMEA (600) | 5.9 | 0.18 | rectangular |
| I-11 | Polymer 11 (80) | PAG 1 (2) | — | TBA (0.125) | PGMEA (600) | 6.1 | 0.18 | rectangular |
| I-12 | Polymer 12 (80) | PAG 1 (2) | — | TBA (0.125) | PGMEA (600) | 6.1 | 0.18 | rectangular |
| I-13 | Polymer 13 (80) | PAG 1 (2) | — | TBA (0.125) | PGMEA (600) | 6.0 | 0.20 | rectangular |
| I-14 | Polymer 14 (80) | PAG 1 (2) | — | TBA (0.125) | PGMEA (600) | 6.0 | 0.18 | rectangular |
| I-15 | Polymer 15 (80) | PAG 1 (2) | — | TBA (0.125) | PGMEA (600) | 5.9 | 0.18 | rectangular |
| I-16 | Polymer 16 (80.) | PAG 1 (2) | — | TBA (0.125) | PGMEA (600) | 5.9 | 0.18 | rectangular |
| I-17 | Polymer 17 (80) | PAG 1 (2) | — | TBA (0.125) | PGMEA (600) | 5.8 | 0.18 | rectangular |
| I-18 | Polymer 18 (80) | PAG 1 (2) | — | TBA (0.125) | PGMEA (600) | 6.0 | 0.18 | rectangular |
| I-19 | Polymer 19 (80) | PAG 1 (2) | — | TBA (0.125) | PGMEA (600) | 5.9 | 0.20 | rectangular |
| I-20 | Polymer 20 (80) | PAG 1 (2) | — | TBA (0.125) | PGMEA (600) | 5.9 | 0.18 | rectangular |
| I-21 | Polymer 21 (80) | PAG 1 (2) | — | TBA (0.125) | PGMEA (600) | 5.8 | 0.15 | rectangular |
| I-22 | Polymer 22 (80) | PAG 1 (2) | — | TBA (0.125) | PGMEA (600) | 5.7 | 0.18 | rectangular |
| I-23 | Polymer 23 (80) | PAG 1 (2) | — | TBA (0.125) | PGMEA (600) | 5.8 | 0.18 | rectangular |
| I-24 | Polymer 24 (80) | PAG 1 (2) | — | TBA (0.125) | PGMEA (600) | 5.6 | 0.18 | rectangular |
| I-25 | Polymer 25 (80) | PAG 1 (2) | — | TBA (0.125) | PGMEA (600) | 5.5 | 0.20 | rectangular |
| I-26 | Polymer 26 (80) | PAG 1 (2) | — | TBA (0.125) | PGMEA (600) | 5.5 | 0.18 | rectangular |
| I-27 | Polymer 27 (80) | PAG 1 (2) | — | TBA (0.125) | PGMEA (600) | 6.7 | 0.18 | rectangular |
| I-28 | Polymer 28 (80) | PAG 1 (2) | — | TBA (0.125) | PGMEA (600) | 6.6 | 0.18 | rectangular |
| I-29 | Polymer 29 (80) | PAG 1 (2) | — | TBA (0.125) | PGMEA (600) | 6.4 | 0.18 | rectangular |
| I-30 | Polymer 30 (80) | PAG 1 (2) | — | TBA (0.125) | PGMEA (600) | 6.1 | 0.18 | rectangular |
| I-31 | Polymer 31 (80) | PAG 1 (2) | — | TBA (0.125) | PGMEA (600) | 6.0 | 0.18 | rectangular |
| I-32 | Polymer 32 (80) | PAG 1 (2) | — | TBA (0.125) | PGMEA (600) | 5.8 | 0.15 | rectangular |

TABLE 2

| Example | Base resin | Photoacid generator | Dissolution inhibitor | Basic compound | Solvent | Sensitivity | Resolution | Shape |
|---|---|---|---|---|---|---|---|---|
| I-33 | Polymer 33 (80) | PAG 1 (2) | — | TBA (0.125) | PGMEA (600) | 6.8 | 0.18 | rectangular |
| I-34 | Polymer 34 (80) | PAG 1 (2) | — | TBA (0.125) | PGMEA (600) | 6.7 | 0.18 | rectangular |
| I-35 | Polymer 35 (80) | PAG 1 (2) | — | TBA (0.125) | PGMEA (600) | 6.5 | 0.18 | rectangular |
| I-36 | Polymer 36 (80) | PAG 1 (2) | — | TBA (0.125) | PGMEA (600) | 6.3 | 0.18 | rectangular |
| I-37 | Polymer 37 (80) | PAG 1 (2) | — | TBA (0.125) | PGMEA (600) | 6.3 | 0.18 | rectangular |
| I-38 | Polymer 38 (80) | PAG 1 (2) | — | TBA (0.125) | PGMEA (600) | 6.2 | 0.18 | rectangular |
| I-39 | Polymer 39 (80) | PAG 1 (2) | — | TBA (0.125) | PGMEA (600) | 6.2 | 0.18 | rectangular |
| I-40 | Polymer 40 (80) | PAG 1 (2) | — | TBA (0.125) | PGMEA (600) | 5.5 | 0.15 | rectangular |

TABLE 2-continued

| Example | Base resin | Photoacid generator | Dissolution inhibitor | Basic compound | Solvent | Sensitivity | Resolution | Shape |
|---|---|---|---|---|---|---|---|---|
| I-41 | Polymer 1 (80) | PAG 1 (2) | — | TEA (0.125) | PG/EL (600) | 6.7 | 0.15 | rectangular |
| I-42 | Polymer 1 (80) | PAG 2 (2) | — | TEA (0.125) | PG/EL (600) | 3.9 | 0.15 | rectangular |
| I-43 | Polymer 1 (80) | PAG 3 (2) | — | TEA (0.125) | PG/EL (600) | 6.6 | 0.15 | rectangular |
| I-44 | Polymer 1 (80) | PAG 4 (2) | — | TEA (0.125) | PG/EL (600) | 6.5 | 0.18 | rectangular |
| I-45 | Polymer 1 (80) | PAG 5 (2) | — | TEA (0.125) | PG/EL (600) | 6.4 | 0.18 | rectangular |
| I-46 | Polymer 1 (80) | PAG 6 (2) | — | TEA (0.125) | PG/EL (600) | 6.4 | 0.18 | rectangular |
| I-47 | Polymer 1 (80) | PAG 7 (2) | — | TEA (0.125) | PG/EL (600) | 4.2 | 0.15 | rectangular |
| I-48 | Polymer 1 (80) | PAG 8 (2) | — | TEA (0.125) | PG/EL (600) | 3.5 | 0.15 | rectangular |
| I-49 | Polymer 2 (80) | PAG 8 (2) | — | TEA (0.125) | PGMEA (600) | 3.5 | 0.18 | rectangular |
| I-50 | Polymer 2 (80) | PAG 8 (2) | — | TEA (0.125) | PGMEA (600) | 3.7 | 0.15 | rectangular |
| I-51 | Polymer 2 (80) | PAG 8 (2) | — | TMMEA (0.125) | PGMEA (600) | 3.2 | 0.18 | rectangular |
| I-52 | Polymer 2 (80) | PAG 8 (2) | — | TMEMEA (0.125) | PGMEA (600) | 3.0 | 0.18 | rectangular |
| I-53 | Polymer 6 (80) | PAG 8 (2) | — | TBA (0.125) | PGMEA (600) | 3.4 | 0.18 | rectangular |
| I-54 | Polymer 6 (80) | PAG 8 (2) | — | TEA (0.125) | PGMEA (600) | 3.5 | 0.15 | rectangular |
| I-55 | Polymer 6 (80) | PAG 8 (2) | — | TMMEA (0.125) | PGMEA (600) | 3.3 | 0.15 | rectangular |
| I-56 | Polymer 6 (80) | PAG 8 (2) | — | TMEMEA (0.125) | PGMEA (600) | 3.2 | 0.15 | rectangular |
| I-57 | Polymer 21 (80) | PAG 8 (2) | DRR 1 (4) | TBA (0.125) | PGMEA (600) | 3.9 | 0.18 | some positive taper |
| I-58 | Polymer 21 (80) | PAG 8 (2) | DRR 2 (4) | TBA (0.125) | PGMEA (600) | 3.8 | 0.18 | some positive taper |
| I-59 | Polymer 21 (80) | PAG 8 (2) | DRR 3 (4) | TBA (0.125) | PGMEA (600) | 3.8 | 0.18 | some positive taper |
| I-60 | Polymer 21 (80) | PAG 8 (2) | DRR 4 (4) | TBA (0.125) | PGMEA (600) | 3.2 | 0.15 | rectangular |
| I-61 | Polymer 29 (80) | PAG 2 (1) PAG 8 (1) | — | TBA (0.125) | PGMEA (600) | 3.3 | 0.15 | rectangular |
| I-62 | Polymer 32 (80) | PAG 2 (1) PAG 8 (1) | — | TBA (0.125) | PGMEA (600) | 3.1 | 0.15 | rectangular |
| I-63 | Polymer 35 (80) | PAG 8 (2) | ACC 1 (6) | TBA (0.125) | PGMEA (600) | 3.4 | 0.18 | rectangular |
| I-64 | Polymer 38 (80) | PAG 8 (2) | ACC 1 (6) | TBA (0.125) | PGMEA (600) | 3.3 | 0.18 | rectangular |

TABLE 3

| Example | Base resin | Photoacid generator | Dissolution inhibitor | Basic compound | Solvent | Sensitivity | Resolution | Shape |
|---|---|---|---|---|---|---|---|---|
| I-65 | Polymer 29 (40) Polymer 40 (40) | PAG 8 (2) | — | TEA (0.125) | PGMEA (600) | 3.4 | 0.15 | rectangular |
| I-66 | Polymer 32 (4) Polymer 39 (40) | PAG 8 (2) | — | TEA (0.125) | PGMEA (600) | 3.0 | 0.15 | rectangular |
| I-67 | Polymer 30 (40) | PAG 8 (2) | — | TEA (0.125) | PGMEA (600) | 3.3 | 0.15 | rectangular |

TABLE 3-continued

| Example | Base resin | Photoacid generator | Dissolution inhibitor | Basic compound | Solvent | Sensitivity | Resolution | Shape |
|---|---|---|---|---|---|---|---|---|
| I-68 | Polymer 41 (40) Polymer 32 (40) | PAG 8 (2) | — | TEA (0.125) | PGMEA (600) | 3.3 | 0.15 | rectangular |
| I-69 | Polymer 41 (40) Polymer 36 (40) | PAG 8 (2) | — | TEA (0.125) | PGMEA (600) | 4.2 | 0.18 | rectangular |
| I-70 | Polymer 42 (40) Polymer 38 (40) Polymer 42 (40) | PAG 8 (2) | — | TEA (0.125) | PGMEA (600) | 3.9 | 0.18 | rectangular |

Examples II-1 to II-40

Evaluation of polymers' etching resistance

Polymers 1 to 40 obtained in the above Synthetic Examples were examined for etching resistance.

Each of Polymers 1 to 40 obtained in Synthetic Examples and a comparative polymer (polymethyl methacrylate, molecular weight 10,000) was dissolved in cyclohexanone, and spin coated onto a silicon wafer to a thickness of 1.0 µm. The coating was baked on a hot plate at 110° C. for 90 seconds. These coatings were etched with a chlorine-base gas or a fluorine-base gas while the etching rate (Å/min) was measured.

The results are shown in Tables 4 and 5 while the settings of the instrument are shown in Table 6. t

TABLE 4

| Example | Resin | Solvent | Chlorine etching | Fluorine etching |
|---|---|---|---|---|
| II-1 | Polymer 1 (80) | cyclohexanone (480) | 1860 | 1760 |
| II-2 | Polymer 2 (80) | cyclohexanone (480) | 1850 | 1830 |
| II-3 | Polymer 3 (80) | cyclohexanone (480) | 1800 | 1750 |
| II-4 | Polymer 4 (80) | cyclohexanone (480) | 1850 | 1840 |
| II-5 | Polymer 5 (80) | cyclohexanone (480) | 1850 | 1810 |
| II-6 | Polymer 6 (80) | cyclohexanone (480) | 1750 | 1700 |
| II-7 | Polymer 7 (80) | cyclohexanone (480) | 1810 | 1780 |
| II-8 | Polymer 8 (80) | cyclohexanone (480) | 1870 | 1810 |
| II-9 | Polymer 9 (80) | cyclohexanone (480) | 1870 | 1790 |
| II-10 | Polymer 10 (80) | cyclohexanone (480) | 1810 | 1700 |
| II-11 | Polymer 11 (80) | cyclohexanone (480) | 1810 | 1820 |
| II-12 | Polymer 12 (80) | cyclohexanone (480) | 1700 | 1720 |
| II-13 | Polymer 13 (80) | cyclohexanone (480) | 1700 | 1760 |
| II-14 | Polymer 14 (80) | cyclohexanone (480) | 1720 | 1770 |
| II-15 | Polymer 15 (80) | cyclohexanone (480) | 1720 | 1770 |
| II-16 | Polymer 16 (80) | cyclohexanone (480) | 1660 | 1730 |
| II-17 | Polymer 17 (80) | cyclohexanone (480) | 1680 | 1740 |
| II-18 | Polymer 18 (80) | cyclohexanone (480) | 1730 | 1800 |
| II-19 | Polymer 19 (80) | cyclohexanone (480) | 1770 | 1800 |
| II-20 | Polymer 20 (80) | cyclohexanone (480) | 1690 | 1820 |
| II-21 | Polymer 21 (80) | cyclohexanone (480) | 1790 | 1800 |
| II-22 | Polymer 22 (80) | cyclohexanone (480) | 1770 | 1780 |
| II-23 | Polymer 23 (80) | cyclohexanone (480) | 1830 | 1770 |
| II-24 | Polymer 24 (80) | cyclohexanone (480) | 1810 | 1790 |
| II-25 | Polymer 25 (80) | cyclohexanone (480) | 1780 | 1770 |
| II-26 | Polymer 26 (80) | cyclohexanone (480) | 1750 | 1750 |
| II-27 | Polymer 27 (80) | cyclohexanone (480) | 1800 | 1750 |
| II-28 | Polymer 28 (80) | cyclohexanone (480) | 1800 | 1750 |
| II-29 | Polymer 29 (80) | cyclohexanone (480) | 1710 | 1770 |
| II-30 | Polymer 30 (80) | cyclohexanone (480) | 1820 | 1830 |
| II-31 | Polymer 31 (80) | cyclohexanone (480) | 1820 | 1830 |
| II-32 | Polymer 32 (80) | cyclohexanone (480) | 1750 | 1750 |

TABLE 5

| Example | Resin | Solvent | Chlorine etching | Fluorine etching |
|---|---|---|---|---|
| II-33 | Polymer 33 (80) | cyclohexanone (480) | 1780 | 1710 |
| II-34 | Polymer 34 (80) | cyclohexanone (480) | 1780 | 1710 |
| II-35 | Polymer 35 (80) | cyclohexanone (480) | 1720 | 1650 |
| II-36 | Polymer 36 (80) | cyclohexanone (480) | 1840 | 1770 |
| II-37 | Polymer 37 (80) | cyclohexanone (480) | 1840 | 1770 |
| II-38 | Polymer 38 (80) | cyclohexanone (480) | 1780 | 1710 |
| II-39 | Polymer 39 (80) | cyclohexanone (480) | 1690 | 1680 |
| II-40 | Polymer 40 (80) | cyclohexanone (480) | 1840 | 1780 |
| Comparison | polymethyl methacrylate (80) | cyclohexanone (480) | 2500 | 2250 |

TABLE 6

| | Chlorine etching | Fluorine etching |
|---|---|---|
| Manufacturer Model | Nichiden Anerba K. K. L451D | Tokyo Electron K. K. TE8500 |
| Gas/flow rate | $Cl_2$ 20 sccm<br>$O_2$ 2 sccm<br>$CHF_3$ 15 sccm<br>$BCl_3$ 100 sccm | $CHF_3$ 7 sccm<br>$CF_4$ 45 sccm<br>$O_2$ 20 sccm<br>Ar 90 sccm |
| RF power | 300 W | 600 W |
| Pressure | 2 Pa | 450 mTorr |
| Temperature | 23° C. | −20° C. |
| Time | 360 sec | 60 sec |

It is seen from Tables 1 to 5 that the resist compositions within the scope of the invention have a high resolution and are highly resistant to etching.

Japanese Patent Application No. 10-270673 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A lactone-containing compound of the following formula (1):

(1)

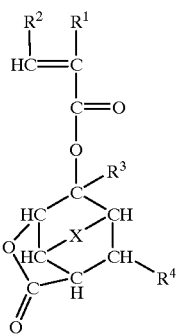

wherein $R^1$ is hydrogen, methyl or $CH_2CO_2R^5$, $R^2$ is hydrogen, methyl or $CO_2R^5$, $R^3$ is hydrogen or a straight, branched or cyclic alkyl group of 1 to 8 carbon atoms, $R^4$ is hydrogen or $CO_2R^5$, $R^5$ is a straight, branched or cyclic alkyl group of 1 to 15 carbon atoms, and X is $CH_2$, $CH_2CH_2$, O or S.

2. A compound of claim 1, wherein in formula (1), $R^3$ is hydrogen or a methyl, ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl or cyclohexylethyl group, and each $R^5$ is independently a methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl or butyladamantyl group.

3. A polymer comprising units of the following formula (1a) and having a weight average molecular weight of 1,000 to 500,000, (1a)

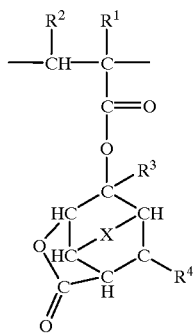

wherein $R^1$ is hydrogen, methyl or $CH_2CO_2R^5$, $R^2$ is hydrogen, methyl or $CO_2R^5$, $R^3$ is hydrogen or a straight, branched or cyclic alkyl group of 1 to 8 carbon atoms, $R^4$ is hydrogen or $CO_2R^5$, $R^5$ is a straight, branched or cyclic alkyl group of 1 to 15 carbon atoms, and X is $CH_2$, $CH_2CH_2$, O or S.

4. A polymer of claim 3, wherein in formula (1a), $R^3$ is hydrogen or a methyl, ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl or cyclohexylethyl group, and each $R^5$ is independently a methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl or butyladamantyl group.

5. A polymer of claim 3, which polymer has a weight average molecular weight of about 3,000 to 100,000.

6. The polymer of claim 3 further comprising units of at least one of the following formulae (2a) to (10a):

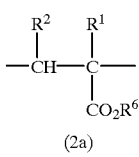 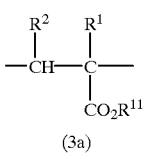 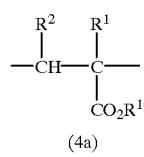

(2a) (3a) (4a)

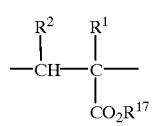 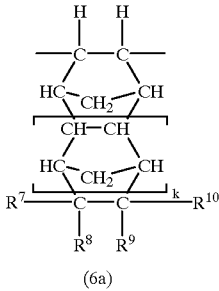

(5a) (6a)

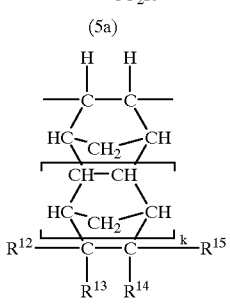 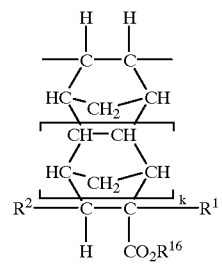

(7a) (8a)

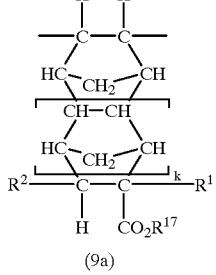 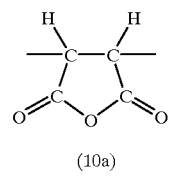

(9a) (10a)

wherein $R^1$ and $R^2$ are as defined above, $R^6$ is hydrogen or a carboxyl or hydroxyl-containing monovalent hydrocarbon group of 1 to 15 carbon atoms, at least one of $R^7$ to $R^{10}$ is a carboxyl or hydroxylcontaining monovalent hydrocarbon group of 1 to 15 carbon atoms, and the remainder are independently hydrogen or a straight, branched or cyclic alkyl group of 1 to 15 carbon atoms, or $R^7$ to $R^{10}$, taken together, may form a ring, and when they form a ring, at least one of $R^7$ to $R^{10}$ is a carboxyl or hydroxyl-containing divalent hydrocarbon group of 1 to 15 carbon atoms, and the remainder are independently a single bond or a straight, branched or cyclic alkylene group of 1 to 15 carbon atoms, $R^{11}$ is a monovalent hydrocarbon group of 3 to 15 carbon atoms containing a —$CO_2$— partial structure, at least one of $R^{12}$ to $R^{15}$ is a monovalent hydrocarbon group of 2 to 15 carbon atoms containing a —$CO_2$— partial structure, and the remainder are independently hydrogen or a straight, branched or cyclic alkyl group of 1 to 15 carbon atoms, or $R^{12}$ to $R^{15}$, taken together, may form a ring, and when they form a ring, at least one of $R^{12}$ to $R^{15}$ is a divalent hydrocarbon group of 1 to 15 carbon atoms containing a —$CO_2$— partial structure, and the remainder are independently a single bond or a straight, branched or cyclic alkylene group of 1 to 15 carbon atoms, $R^{16}$ is a polycyclic hydrocarbon group of 7 to 15 carbon atoms or an alkyl group containing such a polycyclic hydrocarbon group, $R^{17}$ is an acid labile group, and k is equal to 0 or 1.

7. A resist composition, comprising the polymer of claim 3.

8. A resist composition comprising the polymer of claim 3, a photoacid generator capable of generating an acid upon exposure to high-energy radiation or electron beams, and an organic solvent.

9. A resist composition of claim 8, wherein the photoacid generator is an onium salt, a diazomethane or glyoxime derivative or a combination thereof.

10. A resist composition of claim 8, wherein the photoacid generator is provided in the composition in an amount of about 0.1 to 15 parts by weight per 100 parts by weight of the polymer.

11. A resist composition of claim 8, wherein the organic solvent comprises diethylene glycol dimethyl ether, 1-ethoxy-2-propanol or propylene glycol monomethyl ether acetate.

12. A resist composition of claim 8, wherein the solvent is provided in the composition in an amount of 200 to 1000 parts by weight per 100 parts by weight of the polymer.

13. A resist composition of claim 8, which further comprises a dissolution inhibitor.

14. A resist composition of claim 8, which further comprises a basic compound.

15. A resist composition comprising a polymer according to claim 6.

16. A resist composition comprising a polymer according to claim 6, a photoacid generator capable of generating an acid upon exposure to high-energy radiation or electron beams, and an organic solvent.

17. A method for preparing a polymer comprising effecting radical or anionic polymerization between a lactone-containing compound of the general formula (1) and another compound having a carbon-to-carbon double bond

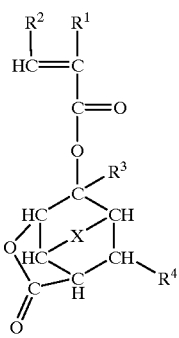

(1)

wherein $R^1$ is hydrogen, methyl or $CH_2CO_2R^5$, $R^2$ is hydrogen, methyl or $CO_2R^5$, $R^3$ is H or a straight, branched or cyclic alkyl group of 1 to 8 carbon atoms, $R^4$ is hydrogen or $CO_2R^5$, $R^5$ is a straight, branched or cyclic alkyl group of 1 to 15 carbon atoms, and X is $CH_2$, $C_2CH_2$, O or S.

18. A method for forming a resist pattern comprising the steps of:

(i) applying a resist composition according to claim 7 onto a substrate to form a film, (ii) heat treating the film and then exposing it to high-energy radiation or electron beams through a photo mask, and (iii) optionally heat treating the exposed film and developing it with a developer.

19. A method for forming a resist pattern comprising the steps of:

(i) applying a resist composition according to claim 8 onto a substrate to form a film, (ii) heat treating the film and then exposing it to high-energy radiation or electron beams through a photo mask, and (iii) optionally heat treating the exposed film and developing it with a developer.

20. A compound of claim 1 wherein $R^3$ is hydrogen.

21. A compound of claim 1 wherein $R^3$ is isopropyl.

* * * * *

UNITED STATES PATENT AND TRADEMARK OFFICE
CERTIFICATE OF CORRECTION

PATENT NO.    : 6,280,898 B1
DATED         : August 28, 2001
INVENTOR(S)   : Koji Hasegawa et al.

It is certified that error appears in the above-identified patent and that said Letters Patent is hereby corrected as shown below:

Column 68,
Line 22, replace "$C_2CH_2$," and replace with -- $CH_2CH_2$ --

Signed and Sealed this

Ninth Day of August, 2005

JON W. DUDAS
*Director of the United States Patent and Trademark Office*

Adverse Decision In Interference

Patent No. Patent No. 6,280,898, Kojihasegawa, Tsunehiro Nishi,Takeshi Kinsho, Jun Hatakeyama, Osamu Watanabe, NOVEL LACTONE-CONTAINING COMPOUNDS, POLYMERS, RESIST COMPOSITIONS, AND PATTERNING METHOD, Interference No. 105,297, final judgment adverse to the patentees rendered, July 15, 2005, as to claims 1-20.

*(Official Gazette, December 20, 2005)*